(12) United States Patent
Mirtich et al.

(10) Patent No.: US 8,582,925 B2
(45) Date of Patent: Nov. 12, 2013

(54) SYSTEM AND METHOD FOR DISPLAYING AND USING NON-NUMERIC GRAPHIC ELEMENTS TO CONTROL AND MONITOR A VISION SYSTEM

(75) Inventors: Brian V. Mirtich, Medfield, MA (US); Andrew Eames, Ashland, MA (US); Brian S. Phillips, Sherborn, MA (US); Robert J. Tremblay, II, Framingham, MA (US); John F. Keating, Madway, MA (US); Steven Whitman, Danville, MA (US)

(73) Assignee: Cognex Technology and Investment Corporation, Mountain View, CA (US)

( * ) Notice: Subject to any disclaimer, the term of this patent is extended or adjusted under 35 U.S.C. 154(b) by 0 days.

(21) Appl. No.: 12/758,455

(22) Filed: Apr. 12, 2010

(65) Prior Publication Data

US 2010/0241981 A1 Sep. 23, 2010

Related U.S. Application Data

(63) Continuation of application No. 10/988,120, filed on Nov. 12, 2004, now Pat. No. 7,720,315.

(51) Int. Cl.
*G06K 9/03* (2006.01)
(52) U.S. Cl.
USPC ............ 382/309; 382/140; 382/141; 345/594
(58) Field of Classification Search
USPC .......... 345/594, 650, 656, 660, 661; 382/140, 382/141, 152, 154, 309, 312; 715/700
See application file for complete search history.

(56) References Cited

U.S. PATENT DOCUMENTS

| 4,214,265 A | 7/1980 | Olesen |
| 4,292,666 A | 9/1981 | Hill et al. |
| 4,384,195 A | 5/1983 | Nosler |
| 4,647,979 A | 3/1987 | Urata |

(Continued)

FOREIGN PATENT DOCUMENTS

| DE | 10012715 | 9/2000 |
| DE | 10040563 | 2/2002 |

(Continued)

OTHER PUBLICATIONS

National Instruments, IMAQ Vision for LabVIEW User Manual, Part No. 371007A-01, Aug. 2004, pp. i, 1-1 to 2-9, 3-2, 3-3, 5-1 & 5-2, http://www.ni.com/pdf/manuals/371007a.pdf.*

(Continued)

*Primary Examiner* — Gregory F Cunningham
(74) *Attorney, Agent, or Firm* — Loginov & Associates, PLLC

(57) ABSTRACT

This invention provides a system and method for employing GUI-based non-numeric slide buttons and bar meters to setup and monitor operating parameters of a vision system. Graphical representations of operating parameters are displayed in a parameter box on the GUI with moving bars that are shaded, patterned or colored so as to provide a relative level between two extremes on a scale of the given operating parameter. Input of operating parameter settings with respect to the scale is made by moving a setting slider along the scale between the extremes. The position of the slider establishes the user-input setting relative to the scale. In an illustrative embodiment, scales, level bars and setting sliders can also be displayed on the image view itself, adjacent to a given image view feature, which is the subject of the scale.

24 Claims, 11 Drawing Sheets

(56) References Cited

U.S. PATENT DOCUMENTS

| | | | |
|---|---|---|---|
| 4,847,772 A | 7/1989 | Michalopoulos et al. | |
| 4,916,640 A | 4/1990 | Gasperi | |
| 4,962,538 A | 10/1990 | Eppler et al. | |
| 4,972,494 A | 11/1990 | White et al. | |
| 5,018,213 A | 5/1991 | Sikes | |
| 5,040,056 A | 8/1991 | Sager et al. | |
| 5,121,201 A | 6/1992 | Seki | |
| 5,146,510 A | 9/1992 | Cox et al. | |
| 5,164,998 A | 11/1992 | Reinsch | |
| 5,177,420 A | 1/1993 | Wada | |
| 5,184,217 A | 2/1993 | Doering | |
| 5,198,650 A | 3/1993 | Wike et al. | |
| 5,210,798 A | 5/1993 | Ekchian et al. | |
| 5,233,541 A | 8/1993 | Corwin et al. | |
| 5,262,626 A | 11/1993 | Goren et al. | |
| 5,286,960 A | 2/1994 | Longacre, Jr. et al. | |
| 5,298,697 A | 3/1994 | Suzuki et al. | |
| 5,317,645 A | 5/1994 | Perozek et al. | |
| 5,345,515 A | 9/1994 | Nishi et al. | |
| 5,365,596 A | 11/1994 | Dante et al. | |
| 5,420,409 A | 5/1995 | Longacre, Jr. et al. | |
| 5,476,010 A | 12/1995 | Fleming et al. | |
| 5,481,712 A | 1/1996 | Silver et al. | |
| 5,581,625 A | 12/1996 | Connell et al. | |
| 5,687,249 A | 11/1997 | Kato | |
| 5,717,834 A | 2/1998 | Werblin et al. | |
| 5,734,742 A | 3/1998 | Asaeda | |
| 5,742,037 A | 4/1998 | Scola et al. | |
| 5,751,831 A | 5/1998 | Ono | |
| 5,802,220 A | 9/1998 | Black et al. | |
| 5,809,161 A | 9/1998 | Auty et al. | |
| 5,825,483 A | 10/1998 | Michael et al. | |
| 5,852,669 A | 12/1998 | Eleftheriadis et al. | |
| 5,872,354 A | 2/1999 | Hanson | |
| 5,917,602 A | 6/1999 | Bonewitz et al. | |
| 5,929,418 A | 7/1999 | Ehrhart et al. | |
| 5,932,862 A | 8/1999 | Hussey et al. | |
| 5,937,096 A | 8/1999 | Kawai | |
| 5,942,741 A | 8/1999 | Longacre et al. | |
| 5,943,432 A | 8/1999 | Gilmore et al. | |
| 5,960,097 A | 9/1999 | Pfeiffer et al. | |
| 5,960,125 A | 9/1999 | Michael et al. | |
| 5,966,457 A | 10/1999 | Lemelson | |
| 6,046,764 A | 4/2000 | Kirby et al. | |
| 6,049,619 A | 4/2000 | Anandan et al. | |
| 6,061,471 A | 5/2000 | Coleman et al. | |
| 6,072,494 A | 6/2000 | Nguyen | |
| 6,072,882 A | 6/2000 | White et al. | |
| 6,075,882 A * | 6/2000 | Mullins et al. | 382/141 |
| 6,078,251 A | 6/2000 | Landt et al. | |
| 6,088,467 A | 7/2000 | Sarpeshkar et al. | |
| 6,115,480 A | 9/2000 | Washizawa | |
| 6,158,661 A | 12/2000 | Chadima, Jr. et al. | |
| 6,160,494 A | 12/2000 | Sodi et al. | |
| 6,161,760 A | 12/2000 | Marrs | |
| 6,169,535 B1 | 1/2001 | Lee | |
| 6,169,600 B1 | 1/2001 | Ludlow | |
| 6,173,070 B1 | 1/2001 | Michael et al. | |
| 6,175,644 B1 | 1/2001 | Scola et al. | |
| 6,175,652 B1 | 1/2001 | Jacobson et al. | |
| 6,184,924 B1 | 2/2001 | Schneider et al. | |
| 6,215,892 B1 | 4/2001 | Douglass et al. | |
| 6,282,462 B1 | 8/2001 | Hopkins | |
| 6,285,787 B1 | 9/2001 | Kawachi et al. | |
| 6,298,176 B2 | 10/2001 | Longacre, Jr. et al. | |
| 6,301,610 B1 | 10/2001 | Ramser et al. | |
| 6,333,993 B1 | 12/2001 | Sakamoto | |
| 6,346,966 B1 | 2/2002 | Toh | |
| 6,347,762 B1 | 2/2002 | Sims et al. | |
| 6,360,003 B1 | 3/2002 | Doi et al. | |
| 6,396,517 B1 | 5/2002 | Beck et al. | |
| 6,396,949 B1 | 5/2002 | Nichani | |
| 6,408,429 B1 | 6/2002 | Marrion et al. | |
| 6,446,868 B1 | 9/2002 | Robertson et al. | |
| 6,483,935 B1 | 11/2002 | Rostami et al. | |
| 6,487,304 B1 | 11/2002 | Szeliski et al. | |
| 6,525,810 B1 | 2/2003 | Kipman | |
| 6,526,156 B1 | 2/2003 | Black et al. | |
| 6,539,107 B1 | 3/2003 | Michael et al. | |
| 6,542,692 B1 * | 4/2003 | Houskeeper | 386/280 |
| 6,545,705 B1 | 4/2003 | Sigel et al. | |
| 6,549,647 B1 | 4/2003 | Skunes et al. | |
| 6,573,929 B1 | 6/2003 | Glier et al. | |
| 6,580,810 B1 | 6/2003 | Yang et al. | |
| 6,587,122 B1 | 7/2003 | King et al. | |
| 6,597,381 B1 | 7/2003 | Eskridge et al. | |
| 6,608,930 B1 | 8/2003 | Agnihotri et al. | |
| 6,618,074 B1 | 9/2003 | Seeley et al. | |
| 6,621,571 B1 | 9/2003 | Maeda et al. | |
| 6,628,805 B1 | 9/2003 | Hansen et al. | |
| 6,629,642 B1 | 10/2003 | Swartz et al. | |
| 6,646,244 B2 | 11/2003 | Aas et al. | |
| 6,668,075 B1 | 12/2003 | Nakamura et al. | |
| 6,677,852 B1 | 1/2004 | Landt | |
| 6,681,151 B1 | 1/2004 | Weinzimmer et al. | |
| 6,741,977 B1 | 5/2004 | Nagaya et al. | |
| 6,753,876 B2 | 6/2004 | Brooksby et al. | |
| 6,761,316 B2 | 7/2004 | Bridgelall | |
| 6,774,917 B1 | 8/2004 | Foote et al. | |
| 6,816,063 B2 | 11/2004 | Kubler | |
| 6,817,982 B2 | 11/2004 | Fritz et al. | |
| 6,825,856 B1 * | 11/2004 | Fazzio et al. | 345/646 |
| 6,891,570 B2 | 5/2005 | Tantalo et al. | |
| 6,919,793 B2 | 7/2005 | Heinrich | |
| 6,944,584 B1 | 9/2005 | Tenney et al. | |
| 6,973,209 B2 | 12/2005 | Tanaka | |
| 6,985,827 B2 | 1/2006 | Williams et al. | |
| 6,987,528 B1 | 1/2006 | Nagahisa et al. | |
| 6,997,556 B2 | 2/2006 | Pfleger | |
| 6,999,625 B1 | 2/2006 | Nelson et al. | |
| 7,062,071 B2 | 6/2006 | Tsujino et al. | |
| 7,066,388 B2 | 6/2006 | He | |
| 7,070,099 B2 | 7/2006 | Patel | |
| 7,085,401 B2 | 8/2006 | Averbuch et al. | |
| 7,088,387 B1 | 8/2006 | Freeman et al. | |
| 7,088,846 B2 | 8/2006 | Han et al. | |
| 7,097,102 B2 | 8/2006 | Patel et al. | |
| 7,175,090 B2 | 2/2007 | Nadabar | |
| 7,181,066 B1 | 2/2007 | Wagman | |
| 7,227,978 B2 | 6/2007 | Komatsuzaki et al. | |
| 7,266,768 B2 * | 9/2007 | Ferlitsch et al. | 715/273 |
| 7,274,808 B2 | 9/2007 | Baharav et al. | |
| 7,280,685 B2 | 10/2007 | Beardsley | |
| 7,604,174 B2 | 10/2009 | Gerst et al. | |
| 7,657,081 B2 | 2/2010 | Blais et al. | |
| 2001/0042789 A1 | 11/2001 | Krichever et al. | |
| 2002/0005895 A1 | 1/2002 | Freeman et al. | |
| 2002/0037770 A1 * | 3/2002 | Paul et al. | 463/36 |
| 2002/0099455 A1 | 7/2002 | Ward | |
| 2002/0122582 A1 | 9/2002 | Masuda et al. | |
| 2002/0177918 A1 | 11/2002 | Pierel et al. | |
| 2002/0181405 A1 | 12/2002 | Ying | |
| 2002/0196336 A1 | 12/2002 | Batson et al. | |
| 2002/0196342 A1 | 12/2002 | Walker et al. | |
| 2003/0062418 A1 | 4/2003 | Barber et al. | |
| 2003/0095710 A1 | 5/2003 | Tessadro | |
| 2003/0113018 A1 | 6/2003 | Nefian et al. | |
| 2003/0120714 A1 | 6/2003 | Wolff et al. | |
| 2003/0137590 A1 | 7/2003 | Barnes et al. | |
| 2003/0201328 A1 | 10/2003 | Jam et al. | |
| 2003/0219146 A1 | 11/2003 | Jepson et al. | |
| 2003/0227483 A1 | 12/2003 | Schultz et al. | |
| 2004/0122306 A1 | 6/2004 | Spoonhower et al. | |
| 2004/0148057 A1 | 7/2004 | Breed et al. | |
| 2004/0218806 A1 | 11/2004 | Miyamoto et al. | |
| 2005/0173633 A1 * | 8/2005 | Tanaka et al. | 250/311 |
| 2005/0226490 A1 | 10/2005 | Phillips et al. | |
| 2005/0254106 A9 | 11/2005 | Silverbrook et al. | |
| 2005/0257646 A1 | 11/2005 | Yeager | |
| 2005/0275728 A1 | 12/2005 | Mirtich et al. | |
| 2005/0275831 A1 | 12/2005 | Silver | |
| 2005/0275833 A1 | 12/2005 | Silver | |
| 2005/0275834 A1 | 12/2005 | Silver | |
| 2005/0276445 A1 | 12/2005 | Silver et al. | |

(56) References Cited

U.S. PATENT DOCUMENTS

| | | | |
|---|---|---|---|
| 2005/0276459 A1 | 12/2005 | Eames et al. |
| 2005/0276460 A1 | 12/2005 | Silver et al. |
| 2005/0276461 A1 | 12/2005 | Silver et al. |
| 2005/0276462 A1 | 12/2005 | Silver et al. |
| 2006/0022052 A1 | 2/2006 | Patel et al. |
| 2006/0107211 A1 | 5/2006 | Mirtich et al. |
| 2006/0107223 A1 | 5/2006 | Mirtich et al. |
| 2006/0131419 A1 | 6/2006 | Nunnink |
| 2006/0133757 A1 | 6/2006 | Nunnink |
| 2006/0146337 A1 | 7/2006 | Hartog |
| 2006/0146377 A1 | 7/2006 | Marshall et al. |
| 2006/0223628 A1 | 10/2006 | Walker et al. |
| 2006/0249581 A1 | 11/2006 | Smith et al. |
| 2006/0283952 A1 | 12/2006 | Wang |
| 2007/0009152 A1 | 1/2007 | Kanda |
| 2007/0146491 A1 | 6/2007 | Tremblay et al. |
| 2007/0181692 A1 | 8/2007 | Barkan et al. |
| 2008/0036873 A1 | 2/2008 | Silver |
| 2008/0063245 A1 | 3/2008 | Benkley et al. |
| 2008/0166015 A1 | 7/2008 | Haering et al. |
| 2008/0167890 A1 | 7/2008 | Pannese et al. |
| 2008/0205714 A1 | 8/2008 | Benkley |
| 2008/0219521 A1 | 9/2008 | Benkley |
| 2008/0285802 A1 | 11/2008 | Bramblet et al. |
| 2009/0273668 A1 | 11/2009 | Mirtich et al. |
| 2010/0318936 A1 | 12/2010 | Tremblay et al. |

FOREIGN PATENT DOCUMENTS

| | | |
|---|---|---|
| EP | 0896290 | 2/1999 |
| EP | 0939382 | 9/1999 |
| EP | 0815688 | 5/2000 |
| EP | 1469420 | 10/2004 |
| EP | 1734456 | 12/2006 |
| GB | 2226130 | 6/1990 |
| GB | 2309078 | 7/1997 |
| JP | 60147602 | 8/1985 |
| JP | 9-288060 | 11/1997 |
| JP | 11-101689 | 4/1999 |
| JP | 2000-84495 | 3/2000 |
| JP | 2000-293694 | 10/2000 |
| JP | 2000-322450 | 11/2000 |
| JP | 2001-109884 | 4/2001 |
| JP | 2001-194323 | 7/2001 |
| JP | 2002-148205 | 5/2002 |
| WO | WO-9609597 | 3/1996 |
| WO | WO-0215120 | 2/2002 |
| WO | WO-02075637 | 9/2002 |
| WO | WO-03102859 | 12/2003 |
| WO | WO-2005050390 | 6/2005 |
| WO | WO-2005124719 | 12/2005 |

OTHER PUBLICATIONS

Apple Computer Inc., Studio Display User's Manual [online], 1998 [Retrieved on Nov. 24, 2010]. Retrieved from the Internet<URL:http://manuals.info.apple.com/en/StudioDisplay_15inchLCDUserManual.PDF>.*

Stauffer, Chris et al., "Tracking-Based Automatic Object Recognition", Artificial Intelligence Laboratory, Massachusetts Institute of Technology, Cambrid e MAhtt .//www.ai.mit.edu (2001),pp. 133-134.*

Cognex VisionPro, Getting Started—QuickStarL Tutorial, Cognex Corporation, 590-6560, Revision 3.5, pp. 69-94, May 2004.

Cognex 3000/4000/5000 Image Processing, Revision 7.4 590-0135 Edge Detection Tool, 1996.

CVL Vision Tools Guide, Cognex MVS-8000 Series, Chapter 5, Symbol Tool, CVL 5.4, Dec. 1999.

Shane C. Hunt, Mastering Microsoft Photodraw 2000, May 21, 1999, Sybex Inc., pp. 131, 132 and 247.

Cognex 4000/5000 SMD Placement Guidance Package, User's Manual, Release 3.8.00, Chapter 15, 590-6168, 1998.

Avalon Vision Solutions, If accuracy matters in your simplest vision applications Use the Validator, 2006.

Baumer Optronic, Technishche Daten, www.baumeroptonic.com, Product Brochure, 6 pages, Apr. 2006.

Cognex Corporation, Screen shot of the CheckMate GUI Ver. 1.6, Jan. 2005.

Cognex Corporation, Sensorpart FA45 Vision Sensor, Sep. 29, 2006.

Vietze, Oliver, Miniaturized Vision Sensors for Process Automation, Jan. 2, 2005.

Integrated Design Tools, High-Speed CMOS Digital Camera, X-Stream Vision User's Manual, 2000.

IO Industries, High Speed Digital Video Recording Software 4.o, IO Industries, Inc.—Ontario, CA, 2002.

Phillip, Kahn, Building Blocks for Computer Vision Systems, IEEE Expert, vol. 8, No. 6, XP002480004, pp. 40-50, Dec. 6, 1993.

Matrox, Interactive Windows Imaging Software for Industrial and Scientific Applications, Inspector 4.0—Matrox imaging, pp. 8, Apr. 15, 2002.

Olympus Industrial, Design Philosophy, i-speed, 2002.

Olympus Industrial, High Speed, High Quality Imaging Systems, i-speed Product Brochure—Publisher Olympus Industrial, 2002.

RVSI, Smart Camera Reader for Directly Marked Data Matrix Codes, HawkEye 1515 with GUI, 2004.

Whelan, P. et al., Machine Vision Algorithms in Java, Chapter 1—An Introduction to Machine Vision, Springer-Verlag, XP002480005, 2001.

Photron, USA, Product information for FASTCAM-X 1280 PCI, Copyright 2004, www.photron.com.

Photon USA, Product Information for FastCAM PCI, Copyright 2004, www.photron.com.

Photron, USA, Product Information for Ultima 1024, Copyright 2004 www.photron.com.

Photron, USA, Product information for Ultima 512, Copyright 2004 www.photron.com.

Photron, USA, Product Information for Ultima APX, Copyright 2004, www.photron.com.

KSV Instruments Ltd. HiSIS 2002—High Speed Imaging System, www.ksvltd.fi, 2004.

ICS 100, Intelligent Camera Sensor, SICK Product Information, SICK Industrial Sensors, 6900 West 110th St, Minneapolis, MN 55438, www.sickusa.com, Jan. 3, 2002.

Matsushita Imagecheckers, NAiS Machine Vision, Matsushita Machine Vision Systems, 2003.

Rohr, K. Incremental Recognition of Pedestrians from Image Sequences, CVPR93, 1993.

Chang, Dingding et al., Feature Detection of Moving Images Using a Hierarchical Relaxation Method, IEECE Trans. Inf. & Syst., vol. E79-D, Jul. 7, 1996.

Zarandy, A. et al., vision Systems Based on the 128X128 Focal Plane Cellular Visual Microprocessor Chips, IEEE. Mar. 2003, III-518-III-521.

SmartCapture Tool, Feature Fact Sheet, Visionx, Inc., www.visionxinc com, 2003.

Wilson, Andrew, CMOS/CCD sensors spot niche applications, Vision Systems, 2003.

Matsushita LightPix AE10, NAiS Machine Vision, Matsushita Machine Vision Systems, 2003.

Corke, Peter I., et al., Real Time Industrial Machine Vision, Electrical Engineering Congress Sydney, Australia, CSIRO Division of Manufacturing Technology, 1994.

Marsh, R. et al., The application of Knowledge based vision to closed-loop control of the injection molding process, SPIE vol. 3164, Faculty of Engineering University of the West of England United Kingdom, 1997, pp. 605-616.

Zarandy, Akos, et al., Ultra-High Frame Rate Focal Plane Image Sensor and Processor, IEEE Sensors Journal, vol. 2, No. 6, 2002.

LM9630 100×128, 580 fps UltraSensitive Monochrome CMOS Image Sensor, National Semiconductor Corp., www.national.com, Rev. 1.0, Jan. 2004.

Analog Devices, Inc., Blackfin Processor Instruction Set Reference, Revision 2.0, Part No. 82-000410-14, May 2003.

(56) References Cited

OTHER PUBLICATIONS

ADSP-BF533 Blackfin Processor Hardware Reference, Analog Devices Inc., Media Platforms and Services Group, Preliminary Revision, Part No. 82-002005-01, Mar. 2003.
National Instruments, IMAQVision Builder Tutorial, IMAQ XP-002356530, http://www.ni.com/pdf/manuals/322228c.pdf, Dec. 2000.
Denis, Jolivet, LabView and IMAQ Vision Builder Provide Automated Visual Builder, LabVIEW, National Instruments, XP002356529, http://www.ni.com/pdf/csrna/us/JNDESWG.pdf, 2001.
Chen, Y.H., Computer vision for General Purpose Visual Inspection: a Fuzzy Logic Approach, Optics and Lasers in Engineering 22, Elsevier Science Limited, vol. 22, No. 3, 1995, pp. 182-192.
Di Mauro, E.C., et al., Check, a generic and specific industrial inspection tool, IEEE Proc.-Vis. Image Signal Process, vol. 143, No. 4, Aug. 27, 1996, pp. 241-249.
Uno, T. et al., A Method of Real-Time Recognition of Moving Objects and its Application, Pattern Recognition: Pergamon Press, vol. 8, pp. 201-208, 1976.
Hearing, N., et al., Visual Event Detection, Kluwer Academic Publisher, Chapter 2, Section 8, 2001.
IBM, Software Controls for Automated Inspection Device Used to Check Interposer Buttons for Defects, IP.com Journal, IP.com Inc., West Henrietts, NY US, Mar. 27, 2003.
Wright, Anne, et al., Congachrome Vision System User's Guide, Newton Research Labs, Manual Edition 2.0, Documents Software Version 26.0, Jun. 3, 1996.
Stemmer Imaging GmbH, Going Multimedia With Common vision Blox, Product News, www.stemmer-imaging.de, Mar. 3, 2004.
Cordin Company, Electronic Imaging Systems, High Speed Imaging Solutions: 200-500 Series Cameras, www.cordin.com, 2004.
Bi-I, AnaLogic Computers Ltd., 2003.
Bi-I, Bio-inspired Real-Time Very High Speed Image Processing Systems, AnaLogic Computers Ltd., http://www.analogic-computers.com/cgi-bin/phprint21.php, 2004.
Cellular device processes at ultrafast speeds, VisionSystems Design, Feb. 2003.
LaVision GMBH, High Speed CCD/CMOS Camera Systems, Overview of State-of-the-Art High Speed Digital Camera Systems, UltraSpeedStar, www.lavision.de, Sep. 24, 2004.
10-K SEC Filing, iQ 180 Products, Adaptive Optics Associates 900 Coles Road, Blackwood, NJ 08012-4683, Dec. 2003.
Laser Scanning Product Guide, Adaptive Optics Associates, Industrial Products and Systems, 900 Coles Road, Blackwood, NJ 08012-4683, Industrial Holographic and Conventional Laser 1D, Omnidirectional Bar Code Scanners, Mar. 2003.
CV-2100 Series, Keyence America, http://www.keyence.com/products/vision/cv_2100_spec.html, High-Speed Digital Machine Vision System, Dec. 29, 2003.
West, Perry C., High-Speed, Real-Time Machine Vision, Imagenation and Automated Vision Systems, Inc., 2001.
Asundi, A., et al., High-Speed TDI Imaging for Peripheral Inspection, Proc. SPIC vol. 2432, Machine Vision Applications in Industrial Inspection IIII, Frederick Y. Wu, Stephen S. Wilson, Eds., Mar. 1995, pp. 189-194.
Baillard, C., et al., Automatic Reconstruction of Piecewise Planar Models from Multiple Views, CVPR, vol. 02, No. 2, 1999, pp. 2559.
Kim, Zuwhan et al., Automatic Description of Complex Buildings with Multiple Images, IEEE 0-7695-0813, 2000, pp. 155-162.
Siemens AG, Simatic Machine Vision, Simatic VS 100 Series, www.siemens.com/machine-vision, Apr. 1, 2003.
Bauberg, A.M. et al., Learning Flexible Models from Image Sequences, University of Leeds, School of Computer Studies, Research Report Series, Report 93.36, Oct. 1993, pp. 1-13.
CCD/CMOS Sensors Spot Niche Application, PennWell Corporation, Vision System Design—Imaging and Machine Vision Technology, (2004).
Cognex Corporation, "VisionPro Getting Started", Revision 3.2, 590-6508, copyright 2003.
Demotte, Donald "Visual Line Tracking", Application Overview & Issues Machine Vision for Robot Guidance Workshop, (May 5, 2004).
HawkEye 1515—Smart Camera Reader for Directly Marked Data Matrix Codes, RVSI 486 Amherst Street, Nashua, NH 03063, (2004).
6,768,414, Jul. 20, 2004, Francis (withdrawn).
Allen-Bradley, Bulletin 2803 VIM Vision Input Module, Cat. No. 2803-VIM2, Printed USA, 1991 (Submitted in 3 parts).
Allen-Bradley, User's Manual, Bulletin 2803 VIM Vision Input Module, Cat. No. 2803-VIM1, 1987 (Submitted in 2 parts).
Allen-Bradley, Bulletin 5370 CVIM Configurable Vision Input Module, User Manual Cat. No. 5370-CVIM, 1995 (Submitted in 3 parts).
Cognex Corporation, 3000/4000/5000 Vision Tools, revision 7.6, p. 590-0136, Chapter 13, 1996.
Cognex Corporation, Cognex 3000/4000/5000, Vision Tools, Revision 7.6, p. 590-0136, Chapter 10, 1996.
Stauffer, Chris et al., "Tracking-Based Automatic Object Recognition", *Artificial Intelligence Laboratory, Massachusetts Institute of Technology*, Cambridge, MA http://www.ai.mit.edu, (2001), pp. 133-134.

\* cited by examiner

SYSTEM AND METHOD FOR DISPLAYING AND USING NON-NUMERIC GRAPHIC ELEMENTS TO CONTROL AND MONITOR A VISION SYSTEM

CROSS-REFERENCE TO RELATED APPLICATIONS

The present application is a continuation of commonly assigned U.S. patent application Ser. No. 10/988,120, which was filed on Nov. 12, 2004, published as U.S. Publication No. US2010-0198375 on Aug. 5, 2010, now U.S. Pat. No. 7,720, 315, by Brian Mirtich for a SYSTEM AND METHOD FOR DISPLAYING AND USING NON-NUMERIC GRAPHIC ELEMENTS TO CONTROL AND MONITOR A VISION SYSTEM and is hereby incorporated by reference.

RELATED APPLICATION

This application is related to co-pending and commonly assigned U.S. patent application Ser. No. 10/865,155, published as U.S. Publication No. US2005-0275831 on Dec. 15, 2005, entitled METHOD AND APPARATUS FOR VISUAL DETECTION AND INSPECTION OF OBJECTS, by William M. Silver, filed Jun. 9, 2004, the teachings of which are expressly incorporated herein by reference.

FIELD OF THE INVENTION

This invention relates to vision systems, and more particularly to Graphical User Interface (GUI) elements for monitoring and controlling such vision systems.

BACKGROUND OF THE INVENTION

Industrial manufacturing relies on automatic inspection of objects being manufactured. One form of automatic inspection that has been in common use for decades is based on optoelectronic technologies that use electromagnetic energy, usually infrared or visible light, photoelectric sensors, and some form of electronic decision making.

One well-known form of optoelectronic automatic inspection uses an arrangement of photodetectors. A typical photodetector has a light source and a single photoelectric sensor that responds to the intensity of light that is reflected by a point on the surface of an object, or transmitted along a path that an object may cross. A user-adjustable sensitivity threshold establishes a light intensity above which (or below which) an output signal of the photodetector will be energized.

One photodetector, often called a gate, is used to detect the presence of an object to be inspected. Other photodetectors are arranged relative to the gate to sense the light reflected by appropriate points on the object. By suitable adjustment of the sensitivity thresholds, these other photodetectors can detect whether certain features of the object, such as a label or hole, are present or absent. A decision as to the status of the object (for example, pass or fail) is made using the output signals of these other photodetectors at the time when an object is detected by the gate. This decision is typically made by a programmable logic controller (PLC), or other suitable electronic equipment.

Automatic inspection using photodetectors has various advantages. Photodetectors are inexpensive, simple to set up, and operate at very high speed (outputs respond within a few hundred microseconds of the object being detected, although a PLC will take longer to make a decision).

Automatic inspection using photodetectors has various disadvantages, however, including:
  Simple sensing of light intensity reflected from a point on the object is often insufficient for inspection. Instead it may be necessary to analyze a pattern of brightness reflected from an extended area. For example, to detect an edge it may be necessary to analyze a pattern of brightness to see if it corresponds to a transition from a lighter to a darker region.
  It may be hard to arrange the photodetectors when many points on an object need to be inspected. Each such inspection point requires the use of a separate photodetector that needs to be physically mounted in such a way as to not interfere with the placement of the other photodetectors. Interference may be due to space limitations, crosstalk from the light sources, or other factors.
  Manufacturing lines are usually capable of producing a mix of products, each with unique inspection requirements. An arrangement of photodetectors is very inflexible, so that a line changeover from one product to another would require the photodetectors to be physically moved and readjusted. The cost of performing a line changeover, and the risk of human error involved, often offset the low cost and simplicity of the photodetectors.
  Using an arrangement of photodetectors requires that objects be presented at known, predetermined locations so that the appropriate points on the object are sensed. This requirement may add additional cost and complexity that can offset the low cost and simplicity of the photodetectors.

Another well-known form of optoelectronic automatic inspection uses a device that can capture a digital image of a two-dimensional field of view (FOV) in which an object to be inspected is located, and then analyze the image and make decisions. Such a device is usually called a machine vision system, or simply a vision system. The image is captured by exposing a two-dimensional array of photosensitive elements for a brief period, called the integration or shutter time, to light that has been focused on the array by a lens. The array is called an imager and the individual elements are called pixels. Each pixel measures the intensity of light falling on it during the shutter time. The measured intensity values are then converted to digital numbers and stored in the memory of the vision system to form the image, which is analyzed by a digital processing element such as a computer, using methods well-known in the art to determine the status of the object being inspected.

In some cases the objects are brought to rest in the field of view, and in other cases the objects are in continuous motion through the field of view. An event external to the vision system, such as a signal from a photodetector, or a message from a PLC, computer, or other piece of automation equipment, is used to inform the vision system that an object is located in the field of view, and therefore an image should be captured and analyzed. Such an event is called a trigger.

Machine vision systems avoid the disadvantages associated with using an arrangement of photodetectors. They can analyze patterns of brightness reflected from extended areas, easily handle many distinct features on the object, accommodate line changeovers through software systems and/or processes, and handle uncertain and variable object locations.

Machine vision systems have disadvantages compared to an arrangement of photodetectors, including:
  They are relatively expensive, often costing ten times more than an arrangement of photodetectors.

They can be difficult to set up, often requiring people with specialized engineering training.

They operate much more slowly than an arrangement of photodetectors, typically requiring tens or hundreds of milliseconds to make a decision. Furthermore, the decision time tends to vary significantly and unpredictably from object to object.

Machine vision systems have limitations that arise because they make decisions based on a single image of each object, located in a single position in the field of view (each object may be located in a different and unpredictable position, but for each object there is only one such position on which a decision is based). This single position provides information from a single viewing perspective, and a single orientation relative to the illumination. The use of only a single perspective often leads to incorrect decisions. It has long been observed, for example, that a change in perspective of as little as a single pixel can in some cases change an incorrect decision to a correct one. By contrast, a human inspecting an object usually moves it around relative to his eyes and the lights to make a more reliable decision.

Also, the limitations of machine vision systems arise in part because they operate too slowly to capture and analyze multiple perspectives of objects in motion, and too slowly to react to events happening in the field of view. Since most vision systems can capture a new image simultaneously with analysis of the current image, the maximum rate at which a vision system can operate is determined by the larger of the capture time and the analysis time. Overall, one of the most significant factors in determining this rate is the number of pixels comprising the imager.

The availability of new low-cost imagers, such as the LM9630 from National Semiconductor of Santa Clara, Calif. that operate at a relatively low-resolution (approximately 100×128 pixels), high frame rate (up to 500 frames per second) and high sensitivity allowing short shutter times with inexpensive illumination (e.g., 300 microseconds with LED illumination), have made possible the implementation of a novel vision detector that employs on-board processors to control machine vision detection and analysis functions. A novel vision detector using such an imager, and overall inspection system employing such a vision detector, is taught in co-pending and commonly assigned U.S. patent application Ser. No. 10/865,155, published as U.S. Publication No. US2005-0275831 on Dec. 15, 2005, entitled METHOD AND APPARATUS FOR VISUAL DETECTION AND INSPECTION OF OBJECTS, by William M. Silver, filed Jun. 9, 2004, and the teachings of which are expressly incorporated herein by reference (herein also termed "above-incorporated-by-reference METHOD AND APPARATUS).

An advantage to the above-incorporated-by-reference detection and inspection METHOD AND APPARATUS is that the vision detector can be implemented within a compact housing that is programmed using a PC or other Human-Machine Interface (HMI) device (via, for example a Universal Serial Bus (USB)), and is then deployed to a production line location for normal runtime operation. The outputs of the apparatus are (in one implementation) a pair of basic High/Low lines indicating detection of the object and whether that object passes or fails based upon the characteristics being analyzed. These outputs can be used (for example) to reject a failed object using a rejection arm mounted along the line that is signaled by the apparatus' output.

By way of example, FIG. 1 shows an illustrative embodiment of a vision detector 100 according to the above-incorporated-by-reference METHOD AND APPARATUS FOR VISUAL DETECTION AND INSPECTION OF OBJECTS inspecting objects on a production line. A conveyor 102 transports objects to cause relative movement between the objects and the field of view (FOV) of vision detector 100. Objects 110, 112, 114, 116 and 118 are shown. In this example, the objects include exemplary features upon which location and inspection are based, including a label 120 and a hole 124. More particularly, the exemplary vision detector 100 detects the presence of an object by visual appearance and inspects it based on appropriate inspection criteria. If an object is defective (such as the label-less object 116), the vision detector 100 sends a signal via link 150 to a reject actuator 170 to remove the object (116) from the conveyor stream. An encoder 180 operatively related to the motion of the conveyor (or other relative motion) sends a signal 160 to the vision detector 100, which uses it to insure proper delay of signal 150 from the encoder count where the object crosses some fixed, imaginary reference point 190, called the mark point. If an encoder is not used, the delay can be based on time instead.

In an alternate example, the vision detector 100 sends signals to a PLC for various purposes, which may include controlling a reject actuator. In another exemplary implementation, suitable in extremely high-speed applications or where the vision detector cannot reliably detect the presence of an object, a photodetector is used to detect the presence of an object and sends a signal to the vision detector for that purpose. In yet another implementation, there are no discrete objects, but rather material flows past the vision detector continuously—for example a web. In this case the material is inspected continuously, and signals are sent by the vision detector to automation equipment, such as a PLC, as appropriate.

Basic to the function of the vision detector 100 in the above-incorporated-by-reference METHOD AND APPARATUS is the ability to exploit the abilities of the imager's quick-frame-rate and low-resolution image capture to allow a large number of image frames of an object passing down the line to be captured and analyzed in real-time. Using these frames, the apparatus' on-board processor can decide when the object is present and use location information to analyze designated areas of interest on the object that must be present in a desired pattern for the object to "pass" inspection.

With brief reference to FIG. 2, a timeline is shown, which illustrates a typical operating cycle for a vision detector in visual event detection mode. A portion 200 of the exemplary timeline corresponds to the inspection of a first object, and contains the capture and analysis of seven frames by the vision detector. A second portion 210 corresponds to the inspection of a second object, and contains five frames.

Boxes labeled "c", such as box 220, represent image capture by the vision detector 100. Boxes labeled "a", such as box 230, represent image analysis. It is desirable that capture "c" of the next image be overlapped with analysis "a" of the current image, so that (for example) analysis step 230 analyzes the image captured in capture step 220. In this timeline, analysis is shown as taking less time than capture, but in general analysis will be shorter or longer than capture depending on the application details. If capture and analysis are overlapped, the rate at which a vision detector can capture and analyze images is determined by the longer of the capture time and the analysis time. This is the "frame rate". The above-incorporated-by-reference METHOD AND APPARATUS allows objects to be detected reliably without a trigger signal, such as that provided by a photodetector.

Each analysis step "a" first considers the evidence that an object is present. Frames where the evidence is sufficient are called active. Analysis steps for active frames are shown with a thick border, for example analysis step 240. In an exemplary implementation, inspection of an object begins when an active frame is found, and ends when some number of consecutive inactive frames are found. In the example of FIG. 2, inspection of the first object begins with the first active frame corresponding to analysis step 240, and ends with two consecutive inactive frames, corresponding to analysis steps 246 and 248. Note that for the first object, a single inactive frame corresponding to analysis step 242 is not sufficient to terminate the inspection.

At the time that inspection of an object is complete, for example at the end of analysis step 248, decisions are made on the status of the object based on the evidence obtained from the active frames. In an exemplary implementation, if an insufficient number of active frames were found then there is considered to be insufficient evidence that an object was actually present, and so operation continues as if no active frames were found. Otherwise an object is judged to have been detected, and evidence from the active frames is judged in order to determine its status, for example pass or fail. A variety of methods may be used to detect objects and determine status within the scope of this example; some are described below and many others will occur to those skilled in the art. Once an object has been detected and a judgment made, a report may be made to appropriate automation equipment, such as a PLC, using signals well-known in the art. In such a case a report step would appear in the timeline. The example of FIG. 5 corresponds instead to a setup such as shown in FIG. 1, where the vision detector is used to control a downstream reject actuator 170 via signal 150. By considering the position of the object in the active frames as it passes through the field of view, the vision detector 100 estimates the mark time 250 and 252 at which the object crosses the mark point 190 (FIG. 1). Note that in cases where an encoder 180 is used, the mark time is actually an encoder count; the reader will understand that time and count can be used interchangeably. A report 260, consisting of a pulse of appropriate duration to the reject actuator 170, is issued after a precise delay 270 in time or encoder count from the mark time 250.

Note in particular that the report 260 may be delayed well beyond the inspection of subsequent objects such as object 110 (FIG. 1). The exemplary vision detector 100 uses well-known first-in first-out (FIFO) buffer methods to hold the reports until the appropriate time.

Once inspection of an object is complete, the vision detector 100 may enter an idle step 280. Such a step is optional, but may be desirable for several reasons. If the maximum object rate is known, there is no need to be looking for an object until just before a new one is due. An idle step will eliminate the chance of false object detection at times when an object couldn't arrive, and will extend the lifetime of the illumination system because the lights can be kept off during the idle step.

The processor of the exemplary METHOD AND APPARATUS is provided with two types of software elements to use in making its decisions: "Locators" that locate the object and "Detectors" that decide whether an object feature is present or absent. The decisions made by both Locators and Detectors are used to judge whether an object is detected and, if so, whether it passes inspection. In one example, Locators can be simply described as a one-dimensional edge detector in a region of interest. The vision detector is configured for locating objects by placing Locators at certain positions in an image where an edge feature of the object can be seen when the object is in the field of view. The Locator can be oriented with respect to the direction the object is moving, and sized to ensure that the edge feature of the object can be located at multiple positions while in the field of view. During analysis, the location of the edge feature of the object within the Locator can be reported, as well as a logical output state that the location is known.

Detectors are vision tools that operate on a region of interest that produce a logical output state that detects the presence or absence of features in an image of the object. The vision detector is configured for detecting features of an object by placing Detectors at certain positions in an image where object features can be seen when the object is located by the Locators. Various types of Detectors can be used, such as Brightness Detectors, Edge Detectors, and Contrast Detectors.

Detectors can be linked to the location of the feature determined by a Locator to further refine the presence detection and inspection of the object. Accordingly, in each frame where the object may be viewed at a different perspective, the location of the object determined by the Locator will be different, and the position of the Detectors in the image can be moved according to the location determined by the Locator. The operation of the vision detector at high frame rates, therefore permits the vision detector to capture and analyze multiple images of the object while it passes through the field of view.

The above-discussion of Locators and Detectors is further illustrated by way of example in FIGS. 3 and 4. FIG. 3, thus, represents an image of the object 110 from FIG. 1, containing label feature 120 and hole feature 124, with superimposed graphics (termed "Photos" in the above-incorporated METHOD AND APPARATUS) representing a region of the frame whose output can be used to base decisions and is displayed (at appropriate time, such as during vision detector setup—see below) as an "image view" on a Human-Machine Interface (HMI) for a user to view and manipulate. See FIG. 1, for example, showing a detachable or remote HMI 194 with Graphical User Interface (GUI) screen 196 and image view window 198 which displays an associated image view (300) of an object (120, for example) within the vision detector's (100) field of view. Accordingly, FIG. 3 represents an image view, showing the object 300 containing an image of a label 310 and a hole 312. The object in this example contains six visible features to be inspected, corresponding to the two exemplary Locators and four Detectors further described below.

The Locator 320 is used to detect and locate the top edge of the object, and the Locator 322 is used to detect and locate the right edge. A Brightness Detector 330 is used to help detect the presence of the object. In this example the background is brighter than the object, and the sensitivity threshold is set to distinguish the two brightness levels, with the logic output inverted to detect the darker object and not the brighter background. Together the Locators 320 and 322, and the Brightness Detector 330, provide the evidence needed to judge that an object has been detected, as further described below. A Contrast Detector 340 is used to detect the presence of the hole 312. When the hole 312 is absent the contrast would be very low, and when present the contrast would be much higher. A Spot Detector could also be used. An Edge Detector 360 is used to detect the presence and position of the label 310. If the label 310 is absent, mis-positioned horizontally, or significantly rotated, the analog output of the Edge Detector would be very low. A Brightness Detector 350 is used to verify that the correct label has been applied. In this example, the correct label is white and incorrect labels are darker colors.

As the object (110 in FIG. 1) moves from left to right through the field of view of the vision detector 100, the Locator 322 tracks the right edge of the object and repositions Brightness Detector 330, Contrast Detector 340, Brightness Detector 350, and Edge Detector 360 to be at the correct position relative to the object. Locator 320 corrects for any variation in the vertical position of the object in the field of view, repositioning the Detectors based on the location of the top edge of the object. In general Locators can be oriented in any direction. A user can manipulate Photos in an image view by using well-known HMI techniques. A Photo can be selected by clicking with a mouse, and its ROI can be moved, resized, and rotated by dragging. Additional manipulations for Locators are described below.

FIG. 4 shows a logic view containing a wiring diagram corresponding to the example setup of FIG. 3. A wiring diagram shows a series of features (termed "Gadgets" in the above-incorporated METHOD AND APPARATUS) 420, 422, 430, 440, 450 and 460 being used to inspect objects and interface to automation equipment, and the connections between logic inputs and outputs of the Gadgets. A wiring diagram may be displayed on an HMI for a user to view and manipulate. A display of Gadgets and their logic interconnections on an HMI is called a logic view. A Locator 420 named "Top", corresponding to Locator 320 in the image view of FIG. 15, is connected to AND Gate 410 by wire 424. Similarly, "Side" Locator 422 corresponding to Locator 322, and "Box" Detector 430, corresponding to Brightness Detector 330, are also wired to AND Gate 410. The logic output of "Box" Detector 430 is inverted, as shown by the small circle 432, and as described above, to detect the darker object against a lighter background. The logic output of AND Gate 410 represents the level of confidence that the top edge of the object has been detected, the right edge of the object has been detected, and the background has not been detected. When confidence is high that all three conditions are true, confidence is high that the object itself has been detected. The logic output of AND Gate 410 is wired to the ObjectDetect Judge 400 to be used as the object detection weight for each frame. Since the logic input to the ObjectDetect Judge in this case depends on the current frame, the vision detector is operating in visual event detection mode. Note, when operating in external trigger mode, an Input Gadget would be wired to ObjectDetect. To operate in continuous analysis mode, nothing would be wired to ObjectDetect.

The choice of Gadgets to wire to ObjectDetect is made by a user based on knowledge of the application. In the example of FIGS. 3 and 4, a user may have determined that detecting just the top and right edges was not sufficient to insure that an object is present. Note that Locator 322 might respond to the label's left edge just as strongly as the object's right edge, and perhaps at this point in the production cycle Locator 320 might occasionally find some other edge in the background. By adding Detector 330, and requiring all three conditions by means of AND Gate 410, object detection is made reliable. In the wiring diagram, Contrast Detector "Hole" 440, corresponding to Contrast Detector 340, Brightness Detector "Label" 450, corresponding to Brightness Detector 350, and Edge Detector "LabelEdge" 460, corresponding to Edge Detector 360, are wired to AND Gate 412. The logic output of AND Gate 412 represents the level of confidence that all three image features have been detected, and is wired to ObjectPass Judge 402 to provide the object pass score for each frame.

The logic output of ObjectDetect Judge 400 is wired to AND Gate 470. The logic output of ObjectPass Judge 402 is inverted (circle 403) and also wired to AND Gate 470. The ObjectDetect Judge is set to "output when done" mode, so a pulse appears on the logic output of ObjectDetect Judge 400 after an object has been detected and inspection is complete. Since the logic output of ObjectPass 402 has been inverted, this pulse will appear on the logic output of AND Gate 470 only if the object has not passed inspection. The logic output of AND Gate 470 is wired to an Output Gadget 480, named "Reject", which controls an output signal from the vision detector than can be connected directly to a reject actuator 170 (FIG. 1). The "Reject" Output Gadget 480 is configured by a user to perform the appropriate delay (270 in FIG. 2) needed by the downstream reject actuator.

To aid the user's understanding of the operation of the exemplary vision detector 100, Gadgets and/or wires can change their visual appearance to indicate fuzzy logic values. For example, Gadgets and/or wires can be displayed red when the logic value is below 0.5, and green otherwise. In FIG. 4, wires 404 and 472 are drawn with dashed lines to indicate a logic value below 0.5, and other wires, for example wire 424, are drawn solid to indicate logic values equal to or greater than 0.5. One skilled in the art will recognize that a wide variety of objects can be detected and inspected by suitable choice, configuration, and wiring of Gadgets. One skilled in the art will also recognize that the Gadget class hierarchy of the above-incorporated-by-reference METHOD AND APPARATUS is only one of many software techniques that could be used to practice this implementation.

The HMI GUI screen 196 used to assist in setup and testing of the vision detector allows for many convenient functions of the vision detector 100 to be manipulated by user with relative ease owing to the highly visual nature of the GUI. In implementing either the above-described vision detector, a more-complex machine vision system, or any other system that requires setup based upon image analysis, it is desirable to make the setup as uncomplicated and user-friendly as possible. Accordingly, use of wide range of features inherent in a GUI is highly desirable. In particular, techniques that allow easier, and more intuitive, manipulation and monitoring of the particular system's operating parameters, such as the relevant values for threshold, operating range and sensitivity for Locators and Detectors, are quite desirable.

SUMMARY OF THE INVENTION

This invention provides a system and method for employing GUI-based non-numeric slide buttons and bar meters to setup and monitor operating parameters of a vision system (the term "vision system" as used herein including the above-described vision detector). Such parameters can include, but are not limited to the threshold at which a feature is activated in viewing an image. Operating parameters also include the underlying range of contrast values and levels of brightness intensities (or by input inversion, the level of darkness) recognized and acted upon by the vision system.

In a broadly defined illustrative embodiment the display and control vision system operating parameters employs a graphical user interface (GUI) that displays an image view of a field of view of a vision system imager The GUI includes a location thereon that displays at least one operating parameter in a "non-numeric" graphical format, which includes a scale having a predetermined area and a moving region that has a distinct appearance with respect to the scale wherein an edge of the moving region defines a level of the operating parameter. A user-movable setting graphic is located with respect to the area of the scale. The setting graphic selectively moves along the scale and provides a boundary through which the moving region crosses when it attains a desired (user-set or machine-set) level of the operating parameter. The vision system responds in a predetermined manner based upon attainment of this boundary-defined level. The graphical format is "non-numeric" in that the representations of the scale, distinct moving region and setting graphic free of entry of numeric data with respect to the operating parameter.

In one embodiment, graphical representations of operating parameters are displayed in a parameter box on the GUI with moving bars that are shaded, patterned or colored so as to provide a relative level between two extremes on a scale of the given operating parameter. The endpoints of the scale can be established by analyzing the relevant extremes on a subject image view. The current level of the given parameter is displayed as a bar that extends a distance along the scale that is proportional to the current level of the parameter along the scale. Input of operating parameter settings with respect to the scale is made by moving a setting slider along the scale between the extremes. The position of the slider establishes the user-input setting relative to the scale. In an illustrative embodiment, scales, level bars and setting sliders can also be displayed on the image view itself, adjacent to a given image view feature, which is the subject of the scale.

In one embodiment, the operating parameters can include activation threshold, brightness and contrast. The non-numeric graphical representations of current readings of these operating parameters by the vision system and sliders for user-setting levels of these operating parameters are displayed selectively in association with discrete graphic features or tools on the image view, such at Locators and Detectors. The graphical representations can be provided in a dialog box that is accessed for the discrete graphic features or tools on the image view and/or can be displayed on the image view itself in a location adjacent to (or otherwise associated with) the discrete graphic features or tools on the image view.

BRIEF DESCRIPTION OF THE DRAWINGS

The invention description below refers to the accompanying drawings, of which.

DETAILED DESCRIPTION OF AN ILLUSTRATIVE EMBODIMENT

Figure 5:
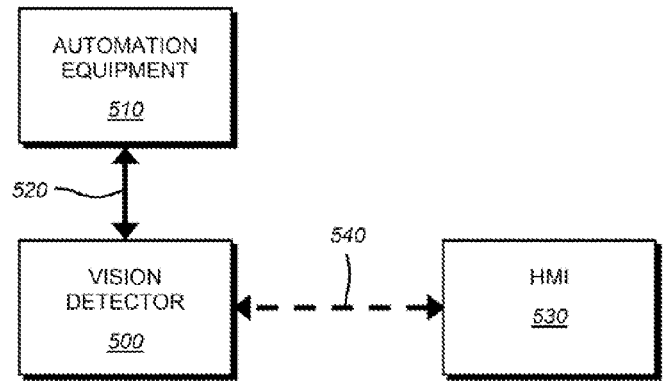
FIG. 5 shows a high-level block diagram for a vision detector in a production environment.

FIG. 5 shows a high-level block diagram for a vision detector 500, which can be used in connection with an embodiment of this invention. The vision detector 500 operates in a production environment. It is expressly contemplated that the teachings of this invention are applicable to any type of vision system that captures and analyzes images of objects and provides a means for monitoring the function of certain operating parameters of the vision system via an HMI. The HMI may be either permanently connected or removable, and where removable, typically is used for setup of operating parameters and monitoring/testing of vision system function based upon the set operating parameters. Thus the vision detector used herein is exemplary of a variety of vision systems that employ settable operating parameters through an HMI.

Figure 1:
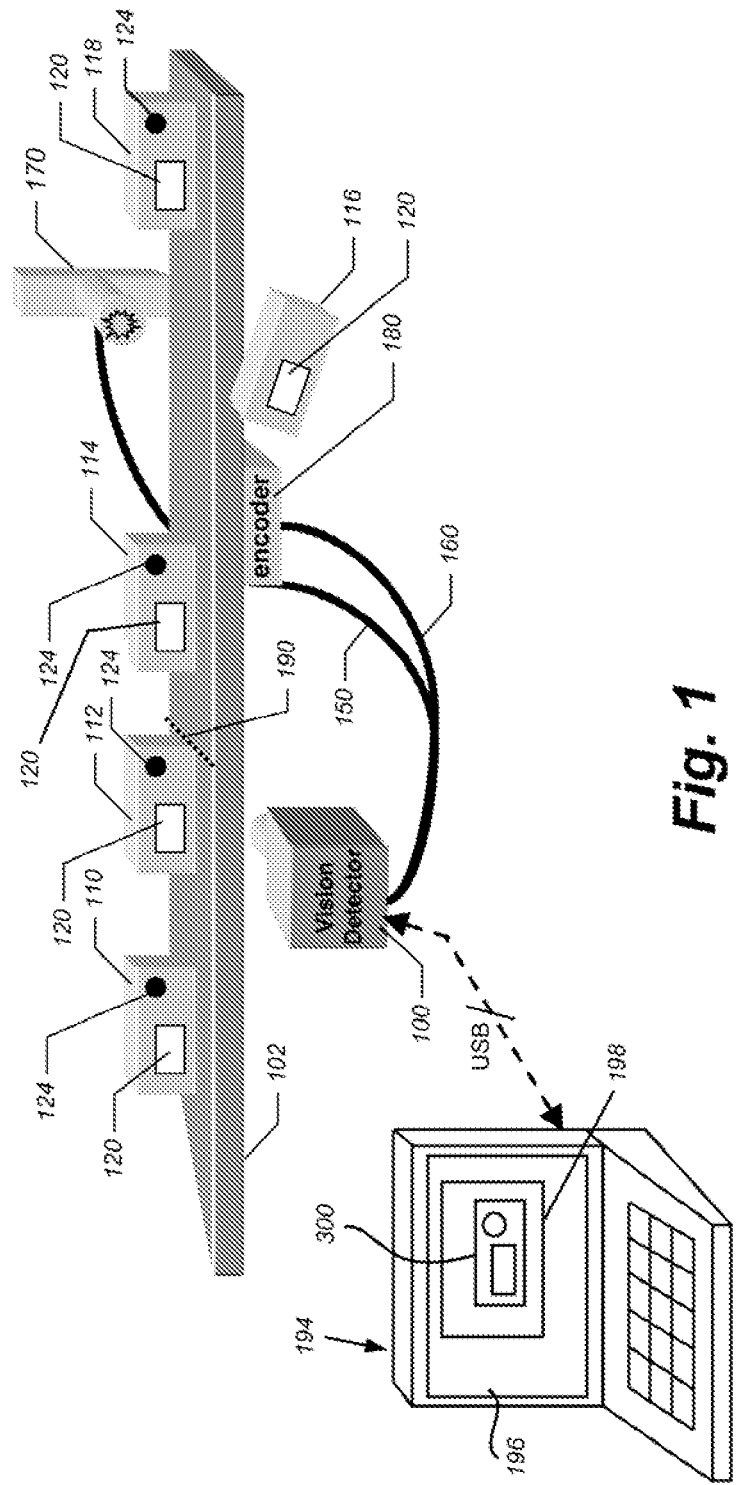
FIG. 1, already described, is a schematic perspective view of an exemplary implementation of a vision detector, inspecting objects on a production line.
Figure 2:
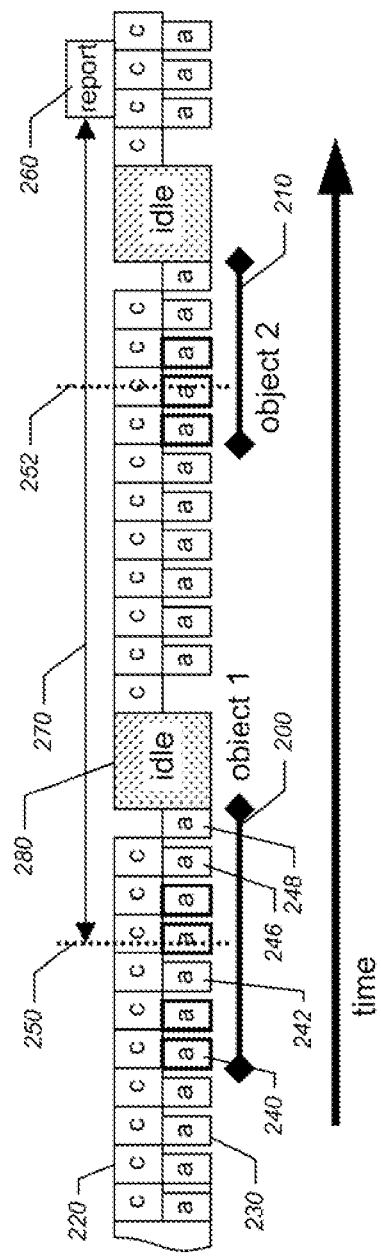
FIG. 2, already described, is a timeline that illustrates a typical operating cycle for the exemplary vision detector of FIG. 1 using visual event detection.
Figure 3:
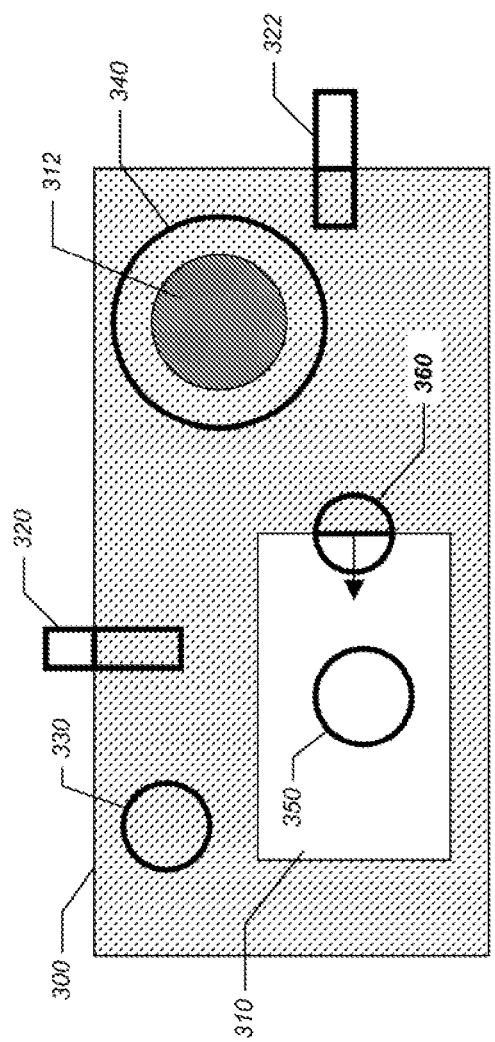
FIG. 3, already described, is an image of an exemplary configuration of the vision detector of FIG. 1 that may be used to inspect an exemplary object.
Figure 4:
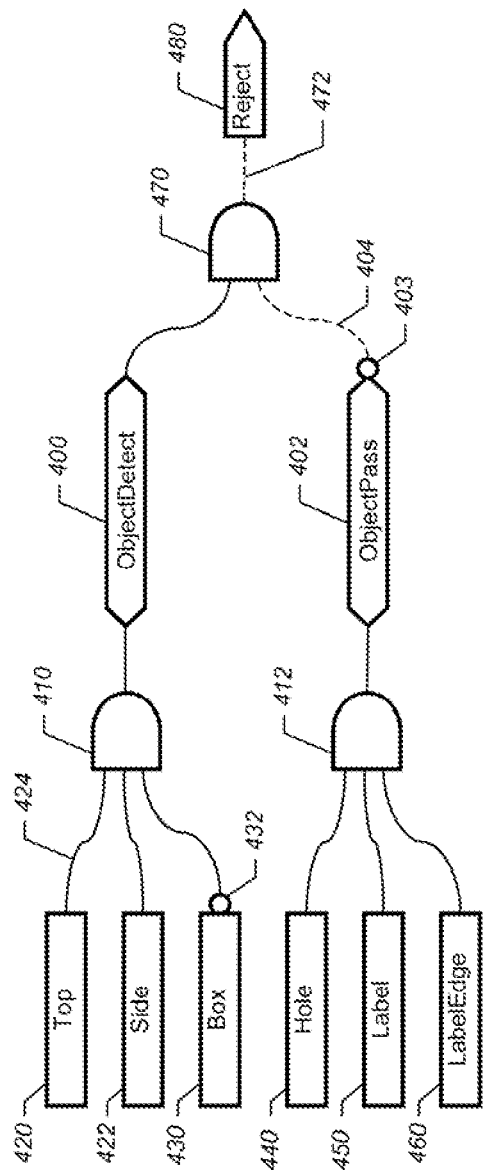
FIG. 4, already described, is a logic diagram of another portion of the configuration corresponding to the exemplary setup of FIG. 3.

The vision detector 500 of this exemplary embodiment functions generally in accordance with principles described in the above-incorporated-by-reference METHOD AND APPARATUS FOR VISUAL DETECTION AND INSPECTION OF OBJECTS, by William M. Silver, and summarized above in connection with the exemplary vision detector 100 (FIG. 1). The vision detector 500 is connected to appropriate automation equipment 510, which may include PLCs, reject actuators, and/or photodetectors, by means of signals 520. The vision detector may also be connected to a Human-Machine Interface (HMI) 530, such as a PC or hand-held device, by means of signals 540. As discussed above the HMI 530 is used for setup, testing and monitoring, and may be removed during normal production use. The various signals 520 and 540 can be implemented in any acceptable format and/or protocol and transmitted in a wired (USB, etc.) or wireless form.

Figure 6:
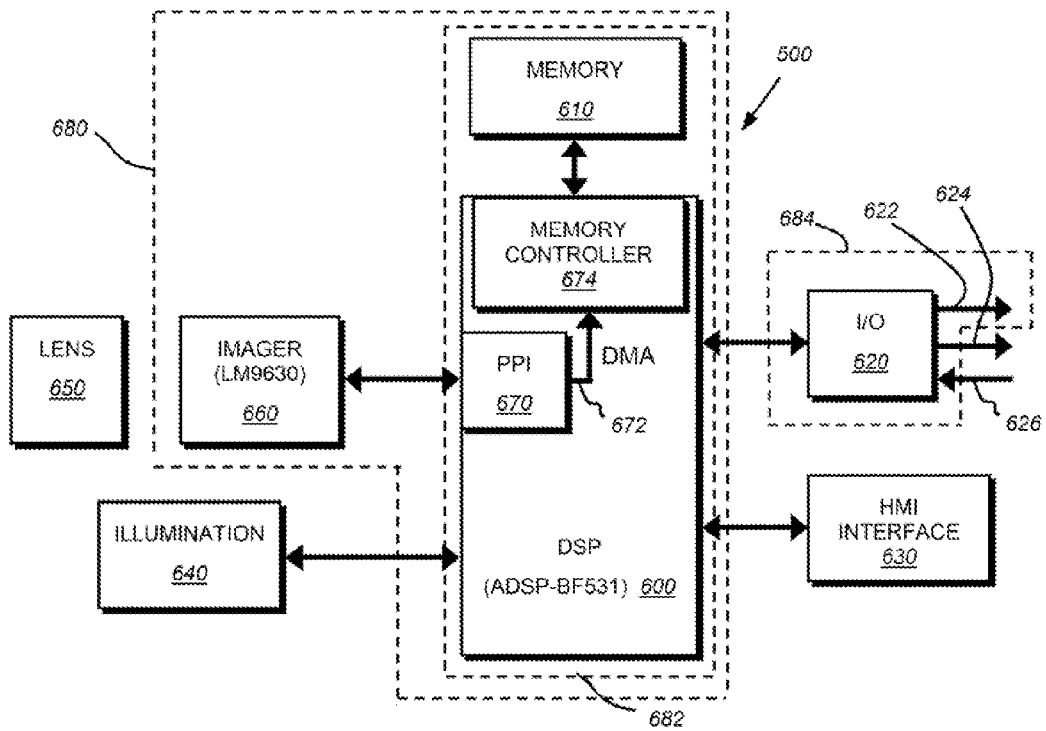
FIG. 6 shows a block diagram of an illustrative embodiment of a vision detector.

FIG. 6 shows a block diagram of an illustrative embodiment of the vision detector 500. A digital signal processor (DSP) 600 runs software to control capture, analysis, reporting, HMI communications, and any other appropriate functions needed by the vision detector. The DSP 600 is interfaced to a memory 610, which includes high-speed random access memory for programs and data and non-volatile memory to hold programs and setup information when power is removed. The DSP 600 is also connected to an I/O module 620 that provides signals to automation equipment, an HMI interface 630, an illumination module 640, and an imager 660. A lens 650 focuses images onto the photosensitive elements of the imager 660.

The DSP 600 can be any device capable of digital computation, information storage, and interface to other digital elements, including but not limited to a general-purpose computer, a PLC, or a microprocessor. It is desirable that the DSP 600 be inexpensive but fast enough to handle a high frame rate. It is further desirable that it be capable of receiving and storing pixel data from the imager simultaneously with image analysis.

In the illustrative embodiment of FIG. 6, the DSP 600 is an ADSP-BF531 manufactured by Analog Devices of Norwood, Mass. In the illustrated arrangement, the Parallel Peripheral Interface (PPI) 670 of the ADSP-BF531 DSP 600 receives pixel data from the imager 660, and sends the data to memory controller 674 via Direct Memory Access (DMA) channel 672 for storage in memory 610. The use of the PPI 670 and DMA 972 allows, under appropriate software control, image capture to occur simultaneously with any other analysis performed by the DSP 600. Software instructions to control the PPI 670 and DMA 672 can be implemented by one of ordinary skill in the art following the programming instructions contained in the ADSP-BF533 Blackfin Processor Hardware Reference (part number 82-002005-01), and the Blackfin Processor Instruction Set Reference (part number 82-000410-14), both incorporated herein by reference. Note that the ADSP-BF531, and the compatible ADSP-BF532 and ADSP-BF533 devices, have identical programming instructions and can be used interchangeably in this illustrative embodiment to obtain an appropriate price/performance tradeoff.

The high frame rate desired by a vision detector suggests the use of an imager unlike those that have been used in prior art vision systems. It is desirable that the imager be unusually light-sensitive, so that it can operate with extremely short shutter times using inexpensive illumination. It is further desirable that it be able to digitize and transmit pixel data to the DSP far faster than prior art vision systems. It is moreover desirable that it be inexpensive and have a global shutter.

These objectives may be met by choosing an imager with much higher light sensitivity and lower resolution than those used by prior art vision systems. In the illustrative embodiment of FIG. 6, the imager 660 is an LM9630 manufactured by National Semiconductor of Santa Clara, Calif. The LM9630 has an array of 128×100 pixels, for a total of 12800 pixels, about 24 times fewer than typical prior art vision systems. The pixels are relatively large at approximately 20 microns square, providing high light sensitivity. The LM9630 can provide 500 frames per second when set for a 300-microsecond shutter time, and is sensitive enough (in most cases) to allow a 300-microsecond shutter using LED illumination. This resolution would be considered far too low for a vision system, but is quite sufficient for the feature detection tasks that are the objectives of the present invention. Electrical interface and software control of the LM9630 can be implemented by one of ordinary skill in the art following the instructions contained in the LM9630 Data Sheet, Rev 1.0, January 2004, which is incorporated herein by reference.

It is desirable that the illumination 640 be inexpensive and yet bright enough to allow short shutter times. In an illustrative embodiment, a bank of high-intensity red LEDs operating at 630 nanometers is used, for example the HLMP-ED25 manufactured by Agilent Technologies. In another embodiment, high-intensity white LEDs are used to implement desired illumination.

In the illustrative embodiment of FIG. 6, the I/O module 620 provides output signals 622 and 624, and input signal 626. One such output signal can be used to provide a signal (150 in FIG. 1) for control of the reject actuator 170. Input signal 626 can be used to provide an external trigger.

As used herein an "image capture device" provides means to capture and store a digital image. In the illustrative embodiment of FIG. 6, the image capture device 680 collectively comprises a DSP 600, imager 660, memory 610, and associated electrical interfaces and software instructions. As used herein, an "analyzer" provides means for analysis of digital data, including but not limited to a digital image. In the illustrative embodiment, the analyzer 682 comprises a DSP 600, a memory 610, and associated electrical interfaces and software instructions. Also as used herein, an "output signaler" provides means to produce an output signal responsive to an analysis. In the illustrative embodiment, the output signaler 684 comprises an I/O module 620 and an output signal 622. It will be understood by one of ordinary skill that there are many alternate arrangements, devices, and software instructions that could be used within the scope of the present invention to implement an image capture device 680, analyzer 682, and output signaler 684.

A variety of engineering tradeoffs can be made to provide efficient operation of an apparatus according to the present invention for a specific application. Consider the following definitions:

b fraction of the field of view (FOV) occupied by the portion of the object that contains the visible features to be inspected, determined by choosing the optical magnification of the lens 650 so as to achieve good use of the available resolution of imager 660;

e fraction of the FOV to be used as a margin of error;

n desired minimum number of frames in which each object will typically be seen;

s spacing between objects as a multiple of the FOV, generally determined by manufacturing conditions;

p object presentation rate, generally determined by manufacturing conditions;

m maximum fraction of the FOV that the object will move between successive frames, chosen based on above values; and r minimum frame rate, chosen based on above values.

From these definitions it can be seen that $$m \le \frac{1-b-e}{n} \quad (1)$$

and $$r \ge \frac{sp}{m} \quad (2)$$

To achieve good use of the available resolution of the imager, it is desirable that b is at least 50%. For dynamic image analysis, n should be at least 2. Therefore, it is further desirable that the object moves no more than about one-quarter of the field of view between successive frames.

In an illustrative embodiment, reasonable values might be b=75%, e=5%, and n=4. This implies that m≤5%, i.e. that one would choose a frame rate so that an object would move no more than about 5% of the FOV between frames. If manufacturing conditions were such that s=2, then the frame rate r would need to be at least approximately 40 times the object presentation rate p. To handle an object presentation rate of 5 Hz, which is fairly typical of industrial manufacturing, the desired frame rate would be at least around 200 Hz. This rate could be achieved using an LM9630 with at most a 3.3-millisecond shutter time, as long as the image analysis is arranged so as to fit within the 5-millisecond frame period. Using available technology, it would be feasible to achieve this rate using an imager containing up to about 40,000 pixels.

With the same illustrative embodiment and a higher object presentation rate of 12.5 Hz, the desired frame rate would be at least approximately 500 Hz. An LM9630 could handle this rate by using at most a 300-microsecond shutter. In another illustrative embodiment, one might choose b=75%, e=15%, and n=5, so that m≤2%. With s=2 and p=5 Hz, the desired frame rate would again be at least approximately 500 Hz.

Having described the general architecture and operation of an exemplary vision system (vision Detector 500) that may support an HMI in accordance with an embodiment of this invention vision, reference is now made to FIG. 7, which shows a diagram of a Graphical User Interface (GUI) screen 700 for a Human-Machine Interface (HMI), interconnected with a vision detector (100) like that shown and described with reference to FIG. 1 above and in connection with the above-incorporated-by-reference METHOD AND APPARATUS FOR VISUAL DETECTION AND INSPECTION OF OBJECTS, by William M. Silver. The screen can reside on any acceptable HMI, including, but not limited to an Laptop Personal Computer (PC); Desktop PC, personal digital assistant or Notebook Computer (for example PC 194) having an appropriate communication link (e.g. USB, wireless, network cable, etc.) with the vision detector (100). An appropriate HMI interface (described in connection with the above-incorporated-by-reference METHOD AND APPARATUS) interconnects with the exemplary vision detector's DSP to allow communication with the HMI. Note that the layout and menu contents of the illustrated screen 700 is exemplary, and a variety of layouts and menu items are contemplated in alternate embodiments. As described above, it is contemplated that the HMI is interconnected to the detector during setup and monitoring or testing. During normal runtime on a production line, the HMI may be disconnected and the detector freely operates various alarms, reject actuators (170) and other interconnected devices, while receiving optical inputs from illuminated objects and electronic inputs from line devices such as the encoder (180).

In this embodiment, the GUI 700 is provided as part of a programming application running on the HMI and receiving interface information from the vision detector. In the illustrative embodiment, a .NET framework, available From Microsoft Corporation of Redmond, Wash., is employed on the HMI to generate GUI screens. Appropriate formatted data is transferred over the link between the vision detector and HMI to create screen displays and populate screen data boxes, and transmit back selections made by the user on the GUI. Techniques for creating appropriate screens and transferring data between the HMI and vision detector's HMI interface should be clear to those of ordinary skill and are described in further detail below.

The screen 700 includes a status pane 702 in a column along the left side. This pane controls a current status box 704, the dialogs for controlling general setup 706, setup of object detection with Locators and Detectors 708, object inspection tool setup 710 and runtime/test controls 712. The screen 700 also includes a right-side column having a pane 720 with help buttons.

The lower center of the screen 700 contains a current selection control box 730. The title 732 of the box 730 relates to the selections in the status pane 702. In this example, the user has clicked select job 734 in the general setup box 706. Note, the general setup box also allows access to an item (736) for accessing a control box (not shown) that enables setup of the imager (also termed "camera"), which includes, entry of production line speed to determine shutter time and gain. In addition, the general setup box allows the user to set up a part trigger (item 738) via another control box (not shown). This may be an external trigger upon which the imager begins active capture and analysis of a moving object, or it may be an "internal" trigger in which the presence of a part is recognized due to analysis of a certain number of captured image frames (as a plurality of complete object image frames are captured within the imager's field of view).

The illustrated select job control box 730 allows the user to select from a menu 740 of job choices. In general, a job is either stored on an appropriate memory (PC or vision detector or is created as a new job. Once the user has selected either a stored job or a new job, the next button accesses a further screen with a Next button 742. These further control boxes can, by default, be the camera setup and trigger setup boxes described above.

Central to the screen 700 is the image view display 750, which is provided above the control box 730 and between the columns 702 and 720 (being similar to image view window 198 in FIG. 1). This display shows a current or stored image frame captured by the vision detector and, essentially, represents the vision detector's current field of view (FOV). In this example, an object 752 is approximately centered in the display. For the purposes of describing the illustrative embodiment, the exemplary object 752 is a bottle on a moving line having a main cylindrical body 754 having a narrowed upper cap section 756 with a series of graphics 758 thereon. Any acceptable object or pattern can be substituted herein and the relative motion between the object and the field of view can be generated by moving the objects, moving the vision detector (or moving its FOV) or moving both the objects and the vision detector. In this example, the object 752 is relative light in surface color/shade. While the background 760 is relatively dark (as depicted by dot shading), in general, there should exist sufficient contrast or shade differences between at least some portions of the object and the background to attain a basis for detecting and inspecting the object. However, it is contemplated that the object may be mostly dark and the background can be lighter in an alternate example.

Figure 7:
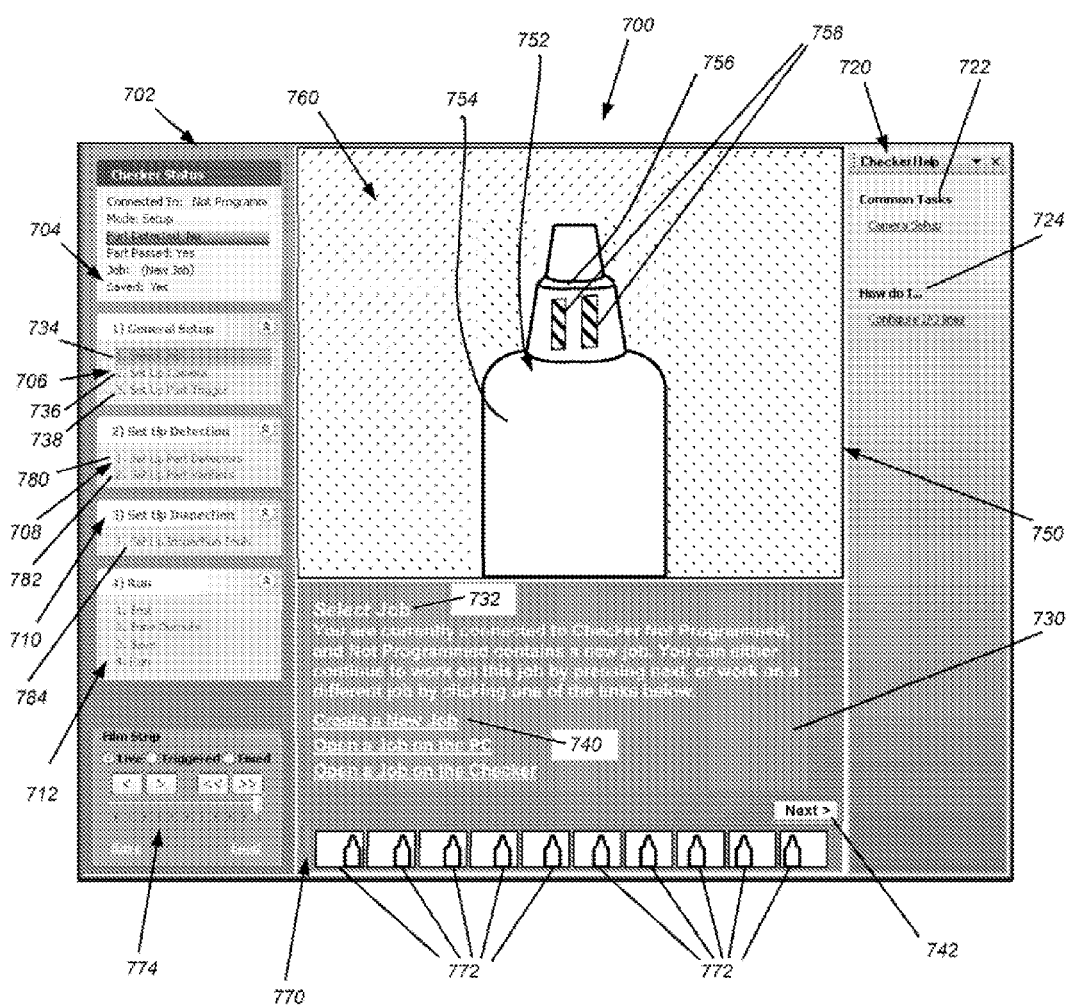
FIG. 7 is a diagram of a Graphical User Interface (GUI) for use with the HMI in accordance with an illustrative embodiment of this invention.

As shown in FIG. 7, the object 752 is either a real-time image being returned from the vision detector under appropriate illumination or it is a stored image. In either case, the image in display 750 is the one upon which setup of the detector is performed. In this example, the object 752 is centered in the display 750 with background space on either side. In other examples, the object may be moved more closely to a side of the display, such as when detection and inspection are based upon internal features located at a distance from an edge.

Before describing further the procedure for manipulating and using the GUI and various non-numeric elements according to this invention, reference is made briefly to the bottommost window 770 which includes a line of miniaturized image frames that comprise a so-called "film strip" of the current grouping of stored, captured image frames 772. These frames 772 each vary slightly in bottle position with respect to the FOV, as a result of the relative motion. The film strip is controlled by a control box 774 at the bottom of the left column.

Figure 8:
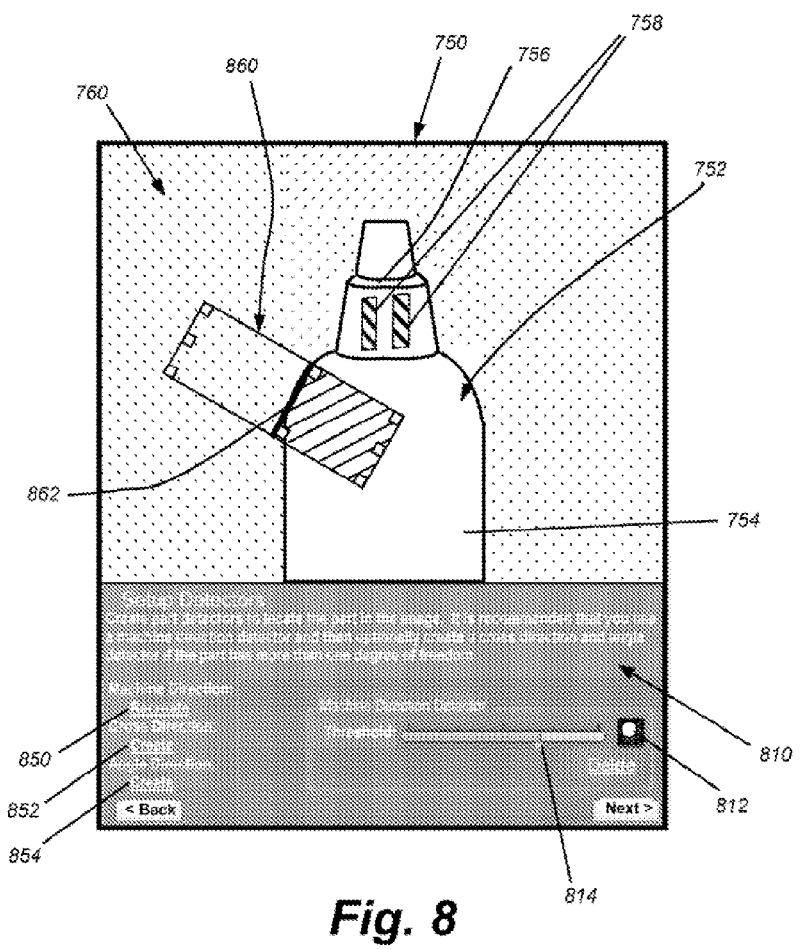
FIG. 8 is a partial view of the diagram of the GUI of FIG. 7 detailing an image view and associated control box with a cursor having automatically placed an edge-detecting Locator of predetermined size and angle on the image view, and an exemplary threshold bar and setting slider within the control box.

Reference is now made to FIG. 8. After performing other general setup functions (see box 706 in FIG. 7), the user may set up the mechanism for detecting the object 752 using the vision detector that is used herein as an example of a "vision system." The user clicks the setup detectors button 780 in FIG. 7 to access the control box 810. Within this box the user may decide which direction he or she wishes to have detection occur. The choices are machine or line-movement direction (typically horizontally or left-to-right/right-to-left across the FOV) (button 850), cross direction (typically vertically or transverse to machine direction) (button 852) or angle direction (button 854). Once a direction is chosen for a main detector (note that additional directions may be chosen by accessing the control box 810 at a later time), the box 810 invites the user to click on a location in the object image, and that click generates a rectangular Locator ROI graphic 860 with an associated plunger 862 that fits to an adjacent edge of the object 752, as shown. A detailed description of an automated system and method for placing and sizing both Locators and Detectors is taught in commonly assigned U.S. Pat. No. 7,636,449, entitled SYSTEM AND METHOD FOR ASSIGNING ANALYSIS PARAMETERS TO A VISION DETECTOR USING A GRAPHICAL INTERFACE, the teachings of which are expressly incorporated herein by reference. The generalized threshold level is also set by the automated process based upon the overall difference between the light and dark pixels along the edge transition adjacent to the Locator 860. In brief summary, the threshold level determines how much transition along an edge or other feature is needed to turn the Locator "on."

Figure 9:
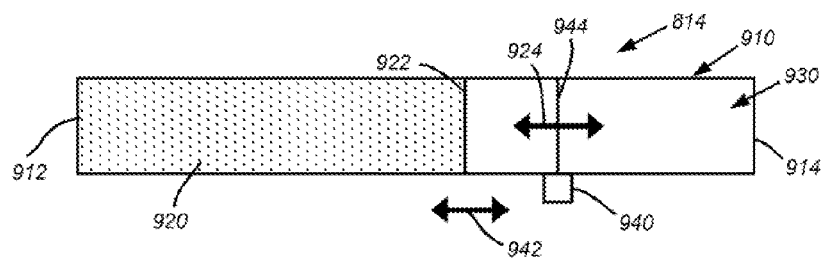
FIG. 9 is a more detailed view of an exemplary non-numeric threshold bar and setting slider for a GUI in accordance with an illustrative embodiment of this invention.

In this example, when the user "clicks" on the cursor placement, the screen presents the control box 810, which now displays an operating parameter box 812. This operating parameter box 812 displays a single non-numeric parameter bar element 814 that reports threshold for the given Locator. Referring to FIG. 9, the bar element 814 is shown in greater detail. In general, the bar element 814 consists of a main bar indicator scale 910 that comprises an elongated rectangular strip spanning between a left end 912 and right end 914. The ends are of arbitrary length and typically sized similarly with other indicator scales in the GUI. That is, each scale is the same length even if one scale shows a value between 50 and 100 and another scale (normally twice as large) shows a value between 0 and 100. Alternatively, the actual size of various scales within the display can vary based upon a number of factors including relative values with respect to other scales. In other words, in an alternate embodiment, a scale between 50 and 100 may appear twice as long in the display as a scale between 0 and 100.

While the scale 910, shown in FIG. 9, is an elongated rectangle, it is expressly contemplated that a "non-numeric" scale or indicator may be expressed as a variety of graphic representations including a gauge meter, pie-chart or graph. It is generally contemplated that any representation for use with a vision system herein define a pair of end points between a minimum and maximum value and that these values be scaled to fit within the confines of the GUI for ease of viewing.

The scale 910 of FIG. 9 displays a moving, distinctly shaded, patterned or colored threshold bar region 920 that extends from the left end 912 to a bar leading edge 922. This region is a proportional representation of the current threshold level on the Locator ROI as read by the vision system. The threshold bar's (920) extension direction (left-to-right) is a convention only, and can be reversed in alternate embodiments. The bar is capable of movement (double arrow 924) across the entire field of the scale 910, depending upon the read level of threshold versus the length (or area) of the overall scale (e.g. the relative value from end 912 to end 914). The area 930 outside the current threshold bar (between the bar leading edge 922 and right scale end 914) appears as a different color, shade or pattern that the user recognizes as open distance between the current threshold level reading and maximum level.

Note that the term "non-numeric" as used herein means that graphically displayed operating parameter level data and controlling graphics can be used to monitor operating parameters of the vision system and to control parameter levels without resort to the entry of numerical data either by direct keying of numbers or other numeric data entry techniques. Rather, the distinctly appearing level bar or region interacts directly with the movable setting graphic (slider) to display and control a given parameter level, and both the level region and setting graphic are similarly proportional to the overall scale.

As also shown in FIG. 9, the bar element 814 includes a graphical representation of a setting slider 940. This slider is movable (double arrow 942) to any location along the scale 910 by a drag and drop function of the GUI cursor. Slider 940 carries with it a transverse boundary line 944, which crosses the scale 910 and that represents the user-defined level of threshold required to trigger the Locator to "locate" the image view edge. Note, the above-incorporated-by-reference SYSTEM AND METHOD FOR ASSIGNING ANALYSIS PARAMETERS TO A VISION DETECTOR USING A GRAPHICAL INTERFACE, provides a procedure for automatically setting the initial threshold level (and associated slider 940) as approximately equal to that of the Locator's plunger 862 in the vicinity of the detected object edge. The indicator bar 920 of the threshold level is generally aligned with the location of the automatically set slider 940 and boundary line 944. However, the user may reset (by sliding) this slider 940 as desired to increase or decrease the required threshold for activating the Locator. When the threshold bar's leading edge 922 crosses the slider boundary line 944, the operating parameter (Locator in this example) is activated.

Figure 10:
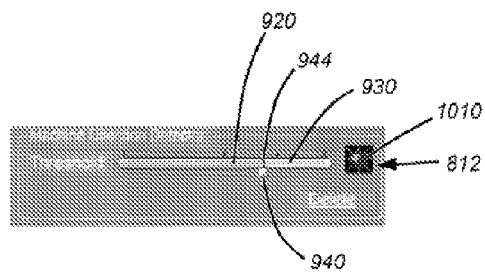
FIG. 10 is a more detailed view of a control box for a GUI containing an exemplary threshold bar and setting slider, in which a desired threshold is attained, in accordance with an illustrative embodiment of this invention.
Figure 11:
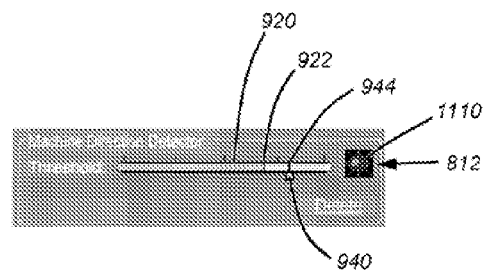
FIG. 11 is a more detailed view of a control box of FIG. 10 containing the exemplary threshold bar and setting slider, in which a desired threshold is not attained, in accordance with an illustrative embodiment of this invention.

By way of example, FIG. 10 shows the operating parameter box 812 with the leading edge (922) of the threshold bar 920 aligned with the boundary line 944 of the setting slider 940. In this embodiment, a threshold-attained indicator 1010 in the operating parameter box 812 is provided. The indicator 1010 displays a bright color (light-green, for example) indicating that the Locator is activated and threshold has been attained. Conversely, in the example of FIG. 11, the leading edge 922 of the threshold bar 920 is placed to the left of the setting slider's boundary line 944, which has been moved to a higher threshold level. Hence the system-read threshold of the image view is insufficient to meet the set threshold. In this example, the threshold-attained indicator 1110 remains dark in this case or displays an alternate color or pattern (such as deep red).

The threshold bar element, and other non-numeric graphical representations of vision system operating parameters herein, are generated by graphic applications that are framed on the HMI. These HMI graphic applications are responsive to numerical values that are typically generated within the processor of the vision system (processor 600 of vision detector 500 in this example). The numerical values in the processor may represent a variety of particular data points (such as pixel intensity, gradient, etc.). These specific data values are appropriately scaled into standardized values that the GUI application expects to receive, and that allow the GUI to readily generate a standard graphical scale therefrom. Similarly GUI transmits back a standard scale of values that the vision system identifies (through handshake, headers or other identifying information) as related to a particular type of vision system data. The vision system thus translates the information into an appropriate set of data that can be meaningfully used by the vision system processor.

Figure 12:
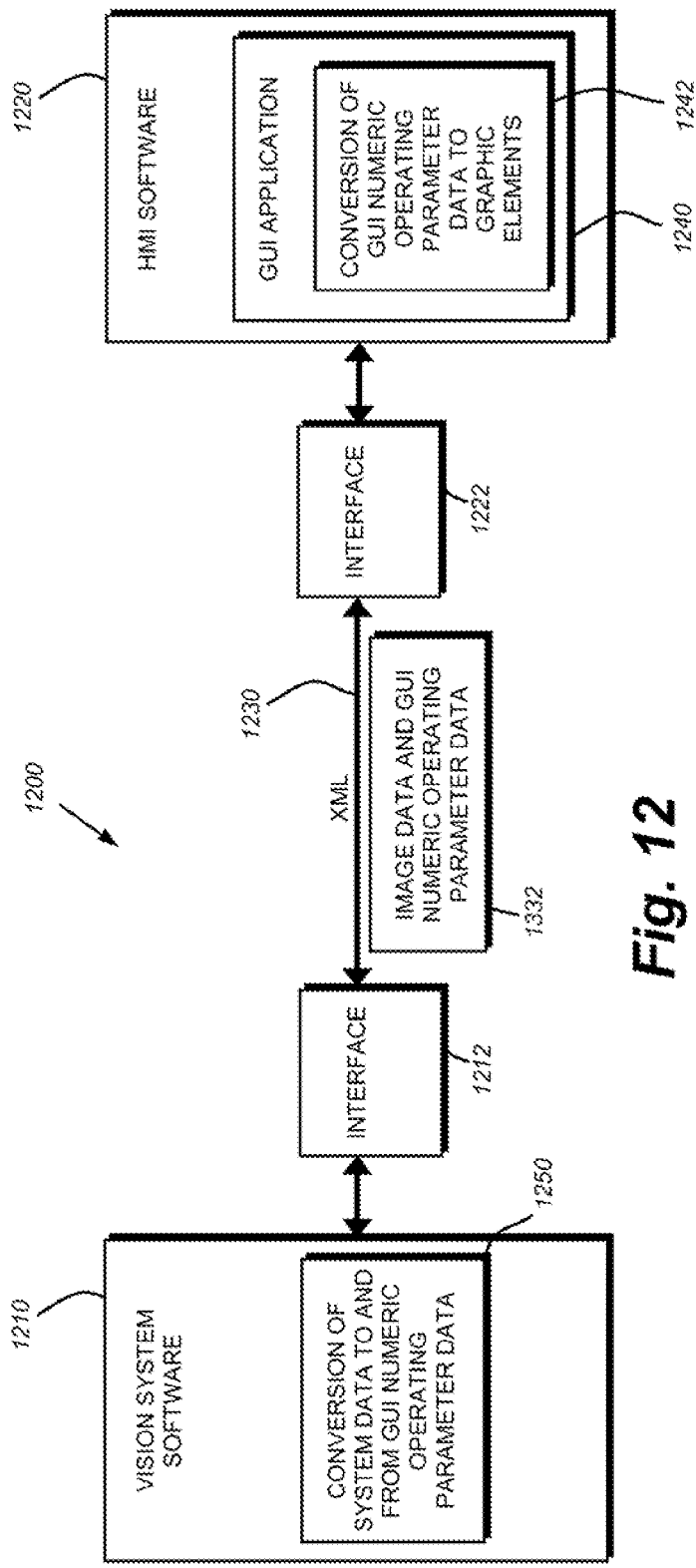
FIG. 12 is a simplified block diagram of a software and communication arrangement for generating and transmitting graphical non-numeric GUI operating parameter data and vision system operating parameter data between an HMI and vision system.

FIG. 12 shows an exemplary block diagram representing an interconnected vision system software layer 1210 and HMI software layer 1220. The layers communicate via respective interfaces 1212 and 1222. The interfaces format data in a link (cable, wireless, etc.) 1230 into an appropriate communication protocol. In this embodiment, the protocol encapsulates a graphical markup language such as HTML or (as shown herein) XML. The transferred data 1232 includes image data and numeric operating parameter data, as well as system control data and other needed information for setting up and monitoring the system. On the HMI side, the software includes an operating system that supports a GUI application 1240. The GUI application can be any acceptable framework including a C++ application, web browser or (according to an illustrative embodiment) a .NET framework. Within the GUI application are standard and user-programmed hooks 1242 that identify data from the vision system as associated with a particular function or GUI box and create the needed graphical representation of levels within the box. The levels are set based upon numeric data transmitted from the vision system that have been formatted to the standards employed by the GUI application. The GUI application also transmits numeric data set to particular levels in its format back to the vision system. In this example, the vision system converts the numeric operating parameter data to and from the GUI-recognized format using a conversion application 1250. By way of example, the GUI expects a value between 0 and 100 for each and every scale. The actual threshold value may have a range from 0 to 255. Thus, when sending a numeric operating parameter value from the vision system to the HMI, the conversion value is multiplied by 100/255 to obtain the scaled, standardized GUI value. Similarly, a GUI value that is returned to the vision system is multiplied by 255/100 in this example. Offset constants and other multipliers may be provided to converted values to determine ranges, etc. In addition, conversion of numeric values from a vision system scale to a GUI scale can be based upon non-linear functions (e.g. logarithms) in certain examples.

Figure 13:
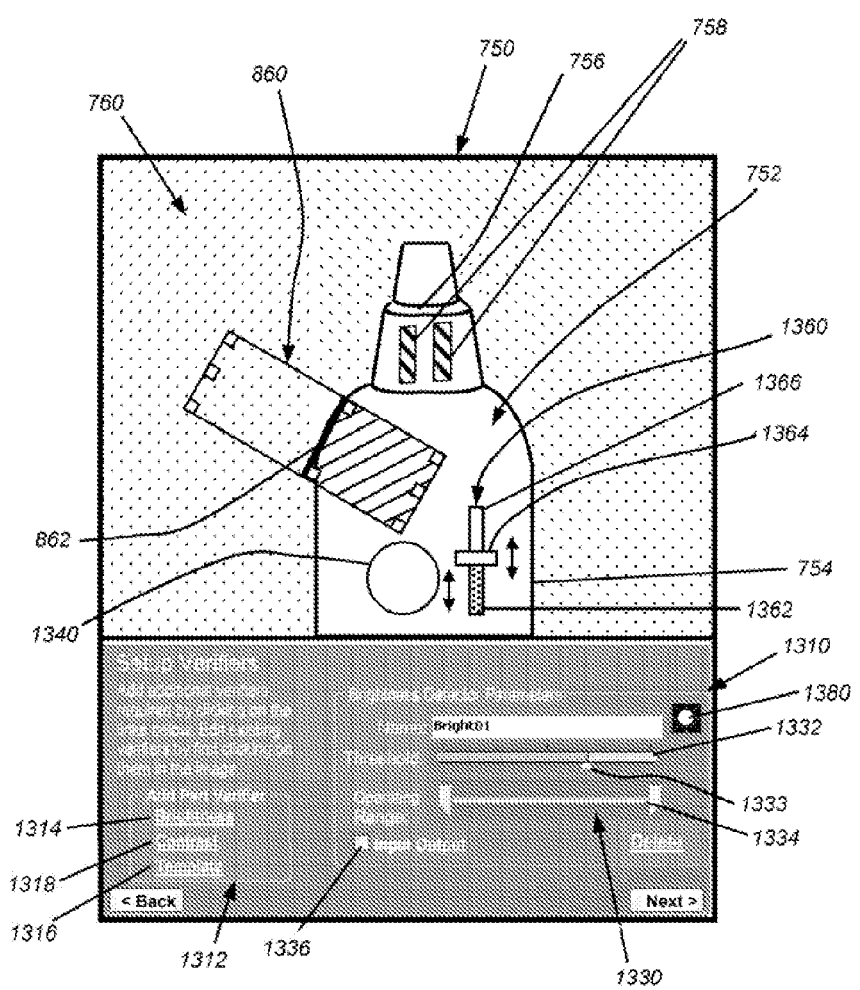
FIG. 13 is a partial view of the diagram of the GUI of FIG. 7 detailing an image view and associated control box with a cursor having automatically placed a brightness-based Detector of predetermined size on the image view, and an exemplary threshold bar with setting slider and brightness range setting slider within the control box.

Reference is now made to a further example in FIG. 13, which shows a partial view of the GUI screen of FIG. 7 with the image view 750 of the object 752. This screen includes a new control box 1310 that provides a menu 1312 of image analysis tool types upon which a detector can be based. In this embodiment, three types of analysis are brightness (button 1314), contrast (button 1316) and trained template (button 1318). It is expressly contemplated that differing or additional analysis tools can be provided in alternate embodiments. In this example, the user has selected brightness (1314) as the type, and a parameter box 1330 appears. Briefly, the parameter box 1330 for brightness displays a threshold bar element 1332 as well as an operating range setting slider 1334. These settings, respectively, control the level of brightness at which detection occurs (threshold) and the general level of brightness used to distinguish the object versus a background. Note that an invert output checkbox 1336, when clicked, allows the user to detect on a darkness threshold rather than brightness.

As shown in FIG. 13, the user has automatically placed and sized a Detector region of interest (ROI) circle 1340 (shown in phantom) using brightness as a detection criterion. This process is further described in the above-incorporated-by-reference SYSTEM AND METHOD FOR ASSIGNING ANALYSIS PARAMETERS TO A VISION DETECTOR USING A GRAPHICAL INTERFACE. This Detector is formed on the object image view in association with the plunger 862 of the locator 860. The diameter of the circle is selected automatically from the center click point based upon placement so that it falls within the desired brightness region of the object. In other words, parts of the ROI that are outside a given brightness range cause the circle to be sized so as to avoid these regions. Similarly to the case of the Locator, the threshold level of a given detector is also estimated and automatically set, subject to subsequent adjustment by the user.

Note that a threshold bar element 1360 is automatically appended to the Detector circle 1340 by the GUI. This allows the user to ascertain the current settings and readings of the particular detector. In this example, the current threshold for the associated Detector 1340 is shown as a shaded, colored or patterned threshold bar 1362 extends along the scale 1366 the current position of the threshold setting slider 1364. These indications correspond with those of the threshold bar 1332 (and threshold setting slider 1333) in the operating parameter box 1330. In this example the threshold has been attained as indicated by the indicator 1380. The representation of threshold data on the image view is particularly helpful where a plurality of detectors are present on the image view, and only one Detector's status is currently shown (typically the last Detector clicked) in the operating parameter box 1330. Note that by clicking any Detector or Locator in the image view, the relevant control box and associated parameter box is retrieved and displayed in the parameter box while the levels of other detectors are continuously displayed on the image view.

Figure 14:
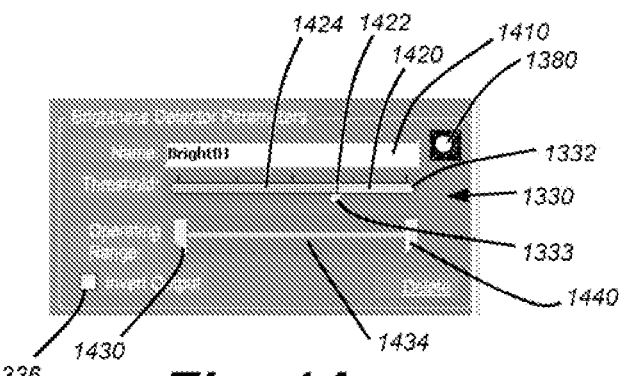
FIG. 14 is a more detailed view of the control box of FIG. 13.

Referring to FIG. 14, the brightness-based operating parameter box 1330 of FIG. 13 is described in further detail. This box contains a title window 1410, which uniquely identifies the Detector, since multiple detectors may be placed on and saved in connection with an image view. Indication and setting of threshold occurs as described above. In general, the scale 1420 represents a total range of brightness recognized by the vision system. The setting slider's boundary line 1422 is aligned with the leading edge of the shaded/colored threshold bar 1242 indicating that the threshold has been attained and the detector positively verifies the object feature of its ROI. In this example, a brightness operating range slider bar 1334 is also provided. This slider includes two setting sliders 1430 and 1340. Each slider may be moved along the bar 1334 to set the range at which brightness is recognized by the brightness tool. On the vision system side, slider settings are converted into numerical offsets from the absolute measured brightness range on the image. For example, if the left slider 1330 is moved halfway across, the range of brightness which the tool recognizes may be moved from the range 0 to 255 to the range 123 to 255.

Figure 15:
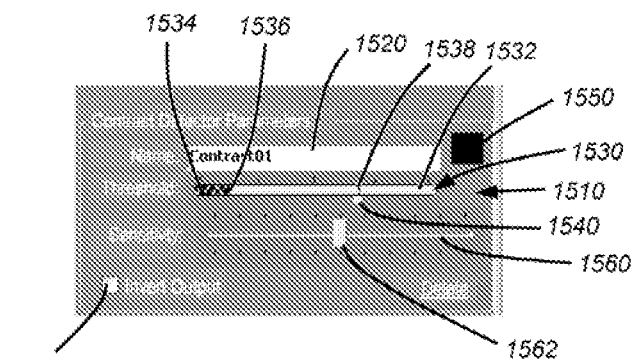
FIG. 15 is a more detailed view of a control box for a contrast-based Detector including an exemplary threshold bar with setting slider and a contrast sensitivity setting slider.

Referring to FIG. 15, the parameter box 1510 for a contrast-based Detector is shown. This parameter box is generated in the GUI by clicking the contrast menu button 1312 in the control box beneath the image view 850 (see menu 1312 in FIG. 13). As shown, the contrast parameter box 1510 includes a name window 1520 that uniquely identifies the Detector associated with the settings of this box. The box 1510 includes a contrast threshold bar element 1530 defining a scale 1532. In this example, the colored or shaded threshold level bar 1534 displays a leading edge 1536 to the left of the setting boundary line 1538 for the setting slider 1538. As such, threshold is not attained and the indicator 1550 is dark.

The contrast parameter box 1510 of FIG. 15 also includes a slider bar 1560 with a moving setting slider 1562. The sensitivity setting slider allows the user to set the desired level of contrast at which threshold is reached. When the slider 1562 is located at the far left, minimal contrast (e.g. ROI is dark in a small region and mostly light) is required to reach threshold. Conversely, when the slider 1562 is located at the far right, significant contrast (half of ROI dark and half of ROI light) is needed to attain threshold. Appropriate numeric values are transmitted from the HMI to the vision system to allow the vision system to compute the level of desired contrast sensitivity. Note that an invert output checkbox 1580 is provided. This allows a mostly dark with minimal light ROI to be used to trigger threshold when sensitivity is minimal.

Figure 16:
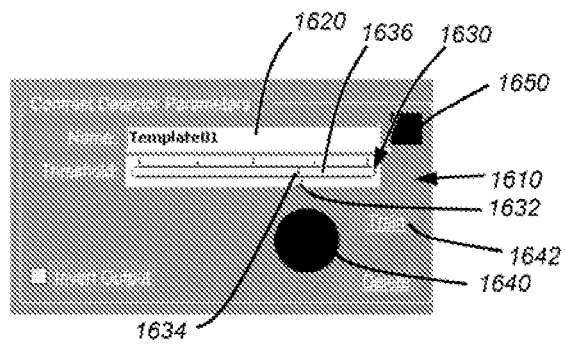
FIG. 16 is a more detailed view of a control box for a trained-template Detector including an exemplary threshold bar with setting slider.

Finally, FIG. 16 shows an operating parameter box 1610 for a Detector based upon a trained template tool. A name window 1620 is provided as above. In this example, the Detector is placed on an ROI of the image view having a particular feature that is easily distinguishable. The threshold bar element 1630 is initially blank as shown. A movable setting slider 1632 and boundary line 1634 are provided in the scale 1636. After training, the feature appears in the now-dark window 1640. Training occurs by clicking the train button 1642. In setup and runtime testing, the trained feature is identified when its threshold meets or exceeds the boundary line 1634. This causes the indicator 1650 to glow brightly. The vision system stores a pattern with particular values and scores. The setting of the threshold by the user signals the vision system as to how accurate the values and scores must be for a given object feature in the ROI to pass.

Hence, the above description provides useful and highly flexible mechanisms for allowing minimally trained persons to quickly employ a vision detector without the need of intensive human programming or labor in setup. While the example of a setup procedure is described above, the non-numeric elements of this invention are displayed and manipulable during a runtime monitoring and testing phase both on the runtime (or played-back, stored) image view and in the control box of the GUI in association with a selected (clicked) image view graphic features or tools (a Detector or Locator in this example).

While the non-numeric graphic elements of this invention are described in association with exemplary image detector tools, such elements can be applied to any vision system that requires monitoring of thresholds and settings, and entry of data that falls within a relative range or scale of values.

The foregoing has been a detailed description of illustrative embodiments of the invention. Various modifications and additions can be made without departing from the spirit and scope thereof. For example, while ROIs for Locators are shown as rectangles and Detectors are shown as circles, their ROIs may each define a different shape or a variety of selectable and/or customized shapes as needed. Likewise, while a particular form of HMI and GUI are shown, a variety of hardware and GUI expressions are expressly contemplated. For example, in alternate embodiments access to operating parameters may be through alternate display screens or boxes. While level bars and sliders are used for graphic representations of data in this description, it is expressly contemplated that such non-numeric graphical representations can be defined by any graphical character or layout on a GUI that shows levels and allows entry of data by altering a filled area of an overall area, representative of an absolute scale between two range extremes. Finally, while the graphic elements shown and described herein are termed "non-numeric," it is expressly contemplated that numeric gradations or labels can be applied to the graphic bars, sliders and other representations as appropriate to assist the user in understanding relative (for example percentages) and actual (for, example pixel intensity) levels for various operating parameters. In general, however, the viewing and setting of levels is accomplished with area-filling (level bars, for example) and movement-based (sliders for example) graphics. Accordingly, this description is meant to be taken only by way of example, and not to otherwise limit the scope of the invention.

The invention claimed is:

1. A method for displaying and controlling vision system operating parameters comprising the steps of:
displaying, on a graphical user interface (GUI) operated by a processor, a plurality of captured images wherein each captured image varies slightly as a result of relative motion within a field of view of a vision system imager;
defining a selected image that is one of the plurality of captured images from a window on the graphical GUI;
applying an automated locator graphic image to a particular location on the selected image in response to user input of clicking on at least a portion of the selected image;
applying one or more automated operating parameters to a desired orientation of the selected image;
defining the automated locator graphic image by at least one user definable operating parameter of the one or more automated operating parameters located in a separate control box displayed on the GUI, the at least one user definable operating parameter being in a non-numeric graphical format that includes a scale having a predetermined area and a user-movable setting graphic having a distinct appearance with respect to the scale; and
setting the user-movable setting graphic of the locator graphic image in response to the user moving the user-movable setting graphic to a desired level of the operating parameter, the user movable setting graphic located with respect to the predetermined area of the scale.

2. The method as set forth in claim 1 wherein the scale comprises a linear bar having a first end point and an opposing second endpoint and the moving region comprises a bar having a leading edge that moves across the scale to define the level of the operating parameter.

3. The method as set forth in claim 2 wherein the user-movable setting graphic comprises a slider graphic located so as to move to setpoints along the linear bar between the first endpoint and the second endpoint.

4. The method as set forth in claim 3 further comprising a non-numeric setting slider that allows a predetermined operating parameter to be set between a first end and a second end of a predetermined operating parameter range.

5. The method as set forth in claim 3 wherein the leading edge defines a level of threshold in the image view at which a predetermined function of the vision system is operating and a boundary defines a desired threshold level at which the predetermined function of the vision system responds.

6. The method as set forth in claim 4 wherein the leading edge defines a level of threshold in the image view at which a predetermined function of the vision system is operating and a boundary defines a desired threshold level at which the predetermined function of the vision system responds.

7. The method as set forth in claim 6 wherein the non-numeric setting slider defines operating levels at which the predetermined function operates.

8. The method as set forth in claim 7 wherein the predetermined function comprises a brightness tool and operating levels comprise a brightness range between two settable brightness range endpoints.

9. The method as set forth in claim 7 wherein the predetermined function comprises a contrast tool and the operating levels comprises a contrast sensitivity that is set within range between zero contrast and maximum contrast.

10. The method as set forth in claim 7 wherein the linear bar is provided in a parameter box at a location in the GUI that is accessed with respect to the predetermined function.

11. The method as set forth in claim 10 further comprising another linear bar having a first end point and an opposing second endpoint and another bar having a leading edge that moves across the scale to define the level of the operating parameter, the linear bar being located on the image view adjacent to a graphical representation on the image view of the predetermined function.

12. A method for displaying and controlling vision system operating parameters comprising the steps of:
    displaying, on a graphical user interface (GUI) operated by a processor, a plurality of captured images;
    enabling selection of at least one image of the plurality of captured images to define a selected image;
    generating an automated locator graphic image that is applied to a particular location on the selected image;
    applying one or more automated operating parameters to a desired orientation of the selected image; and
    providing at least one user definable operating parameter that defines the automated locator graphic image, the at least one user-definable operating parameter being located in a separate control box displayed on the GUI and displayed in a non-numeric graphical format that includes a scale having a predetermined area and a user-movable setting graphic having a distinct appearance with respect to the scale, wherein a feature of the user-movable setting graphic defines a level of the operating parameter.

13. The method of claim 12 wherein each captured image of the plurality of captured images varies slightly as a result of relative motion within a field of view of a vision system imager.

14. The method of claim 12 wherein the step of applying one or more automated operating parameters is performed in response to a user input.

15. The method of claim 12 wherein the step of generating an automated locator graphic that is applied to a particular location on the selected image is performed in response to a user clicking on a feature of the selected image.

16. The method of claim 12 wherein the feature of the selected image is an edge feature.

17. The method of claim 12 wherein the step of applying one or more automated parameters to a desired orientation is in response to a user moving a feature of the selected image to a desired orientation.

18. The method of claim 17 wherein the moving step further comprises dragging, by the user, the feature of the selected image to the desired orientation.

19. The method of claim 1 wherein the defining step is in response to an input, by a user, that selected the image.

20. The method of claim 1 wherein an edge of the user-movable setting graphic defines a level of the operating parameter.

21. The method of claim 14 wherein the user input comprises dragging an edge of the selected image to the desired orientation.

22. A method for displaying and controlling vision system operating parameters comprising the steps of:
    displaying, on a graphical user interface (GUI) operated by a processor, a plurality of captured images within a field of view of a vision system imager;
    receiving a selection of at least one image of the plurality of captured images that defines a selected image;
    generating an automated locator graphic image that is applied to a particular location on the selected image based upon user selection of the particular location;
    applying one or more automated operating parameters to a desired orientation of the selected image in response to a user dragging a feature of the selected image to the desired orientation;
    displaying at least one user definable operating parameter of the one or more automated operating parameters in a separate control box displayed on the GUI, the at least one user definable operating parameter defining the automated locator graphic image and being in a non-numeric graphical format, the at least one user definable operating parameter including a scale and having a predetermined area and a user-movable setting graphic, wherein a feature of the user-movable setting graphic defines a level of the operating parameter; and
    wherein a setting of the user-movable setting graphic of the locator graphic image is set in response to the user moving the user-movable setting graphic to a desired level of the operating parameter.

23. The method of claim 22 wherein the plurality of captured images respectively vary slightly as a result of relative motion within the field of view of the vision system imager.

24. The method of claim 22 wherein the feature of the selected image is an edge feature.

* * * * *